United States Patent
Bowers et al.

(10) Patent No.: US 12,178,891 B2
(45) Date of Patent: Dec. 31, 2024

(54) METHODS AND SYSTEMS FOR PRODUCING, USING, AND ADMINISTERING HYPERPOLARIZED FLUIDS

(71) Applicant: University of Florida Research Foundation, Inc., Gainesville, FL (US)

(72) Inventors: Clifford Russell Bowers, Gainesville, FL (US); Wenbo Zhao, Cambridge (GB)

(73) Assignee: University of Florida Research Foundation, INC., Gainesville, FL (US)

( * ) Notice: Subject to any disclaimer, the term of this patent is extended or adjusted under 35 U.S.C. 154(b) by 279 days.

(21) Appl. No.: 16/753,875

(22) PCT Filed: Oct. 5, 2018

(86) PCT No.: PCT/US2018/054550
§ 371 (c)(1),
(2) Date: Apr. 6, 2020

(87) PCT Pub. No.: WO2019/071090
PCT Pub. Date: Apr. 11, 2019

(65) Prior Publication Data
US 2020/0261606 A1    Aug. 20, 2020

Related U.S. Application Data

(60) Provisional application No. 62/721,655, filed on Aug. 23, 2018, provisional application No. 62/568,825, filed on Oct. 6, 2017.

(51) Int. Cl.
 A61K 49/18   (2006.01)
 G01N 24/08   (2006.01)
 G01R 33/28   (2006.01)
 G01R 33/46   (2006.01)

(52) U.S. Cl.
CPC ....... *A61K 49/1824* (2013.01); *G01N 24/088* (2013.01); *G01R 33/282* (2013.01); *G01R 33/4608* (2013.01)

(58) Field of Classification Search
CPC .. G01R 33/4608; G01R 33/282; G01R 33/62; A61K 49/10; A61K 49/1824; G01N 24/088; G01N 24/12
See application file for complete search history.

(56) References Cited

U.S. PATENT DOCUMENTS

| | | | |
|---|---|---|---|
| 5,860,295 A | 1/1999 | Cates, Jr. et al. | |
| 8,154,284 B2 | 4/2012 | Duckett et al. | |
| 8,961,933 B2 | 2/2015 | Reineri et al. | |
| 9,207,296 B2 | 12/2015 | Bhattacharya et al. | |
| 11,016,152 B2 * | 5/2021 | Chekmenev | G01R 33/282 |
| 2009/0016964 A1 * | 1/2009 | Kalechofsky | A61K 49/1806 424/9.3 |
| 2011/0274626 A1 * | 11/2011 | Duckett | G01R 33/5601 424/9.361 |
| 2015/0217262 A1 | 8/2015 | Wagner et al. | |
| 2016/0274043 A1 | 9/2016 | Lisitza et al. | |
| 2017/0153218 A1 | 6/2017 | Chekmemev et al. | |
| 2020/0132788 A1 | 4/2020 | Chekmenev et al. | |
| 2020/0246491 A1 * | 8/2020 | Iali | A61B 5/055 |

OTHER PUBLICATIONS

Zhao et al., ChemCatChem, 2016, 8, p. 2197-2201. (Year: 2016).*
Zhao et al., Angew. Chem. Int. Ed., 2017, 56, 3925-3929. (Year: 2017).*
Reineri et al., Nature Comm., 2015, p. 1-6. (Year: 2015).*
International Search Report for International Application No. PCT /US2018/054550, mailed Dec. 11, 2018.

* cited by examiner

*Primary Examiner* — Michael G. Hartley
*Assistant Examiner* — Leah H Schlientz
(74) *Attorney, Agent, or Firm* — Thomas | Horstemeyer LLP

(57) ABSTRACT

Methods of and systems for making a hyperpolarized fluid are provided, which include exposing a fluid and parahydrogen to a catalyst. The hyperpolarized fluid can be introduced to a subject. The hyperpolarized fluid can be included in methods of imaging a subject. Also provided are methods that use the hyperpolarized fluids for detecting protein ligand interactions and for enhancing the NMR signals of biopolymers having chemically exchangeable protons.

8 Claims, 17 Drawing Sheets

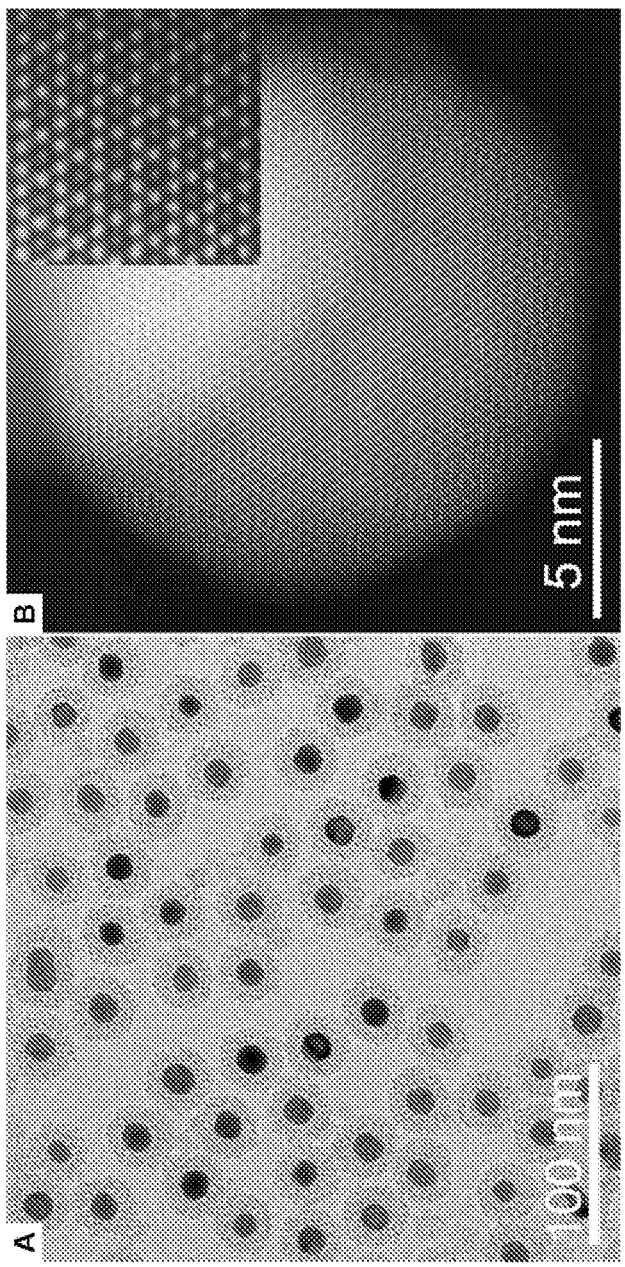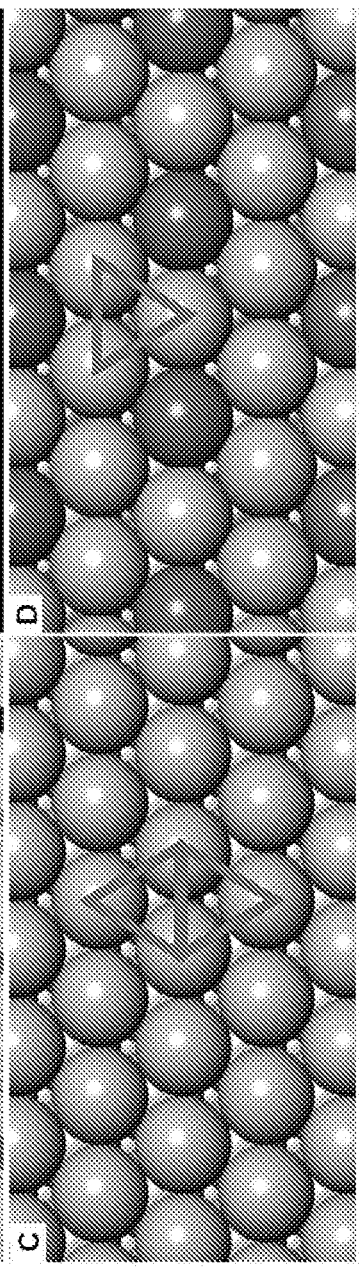
Fig. 1A  Fig. 1B  Fig. 1C  Fig. 1D

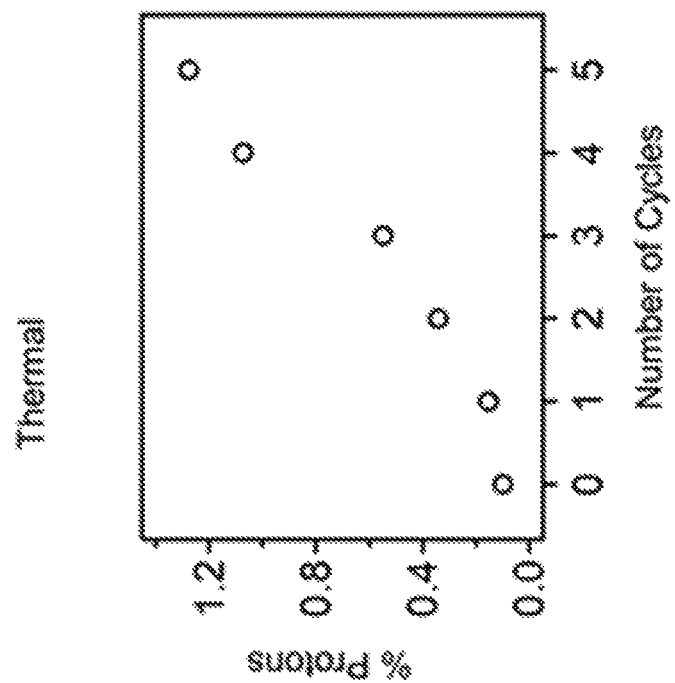
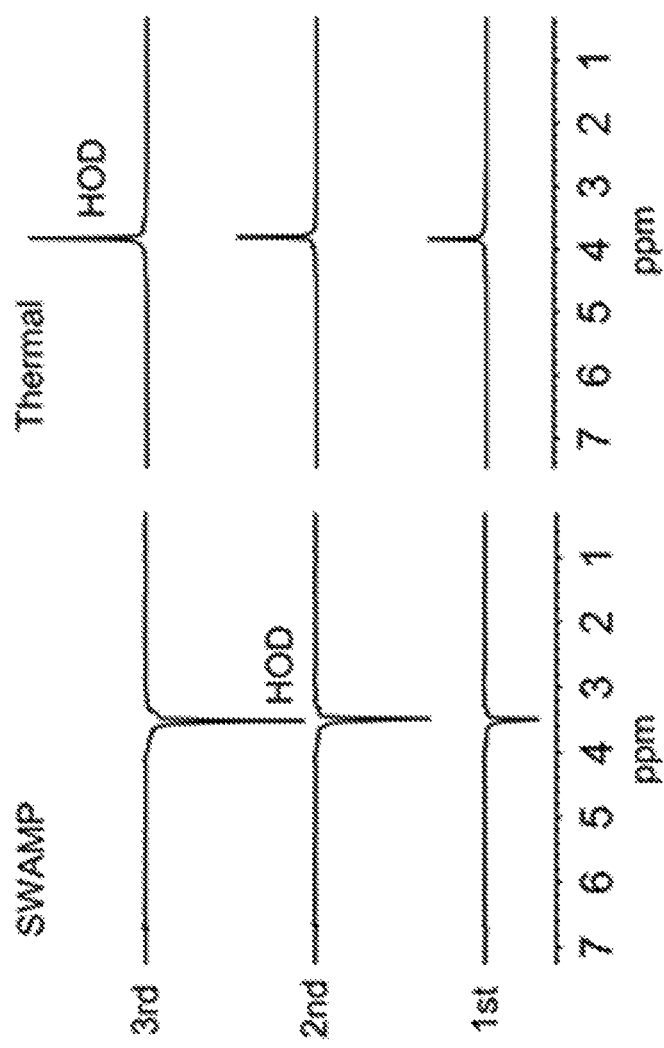
Fig. 13A  Fig. 13B  Fig. 13C

METHODS AND SYSTEMS FOR PRODUCING, USING, AND ADMINISTERING HYPERPOLARIZED FLUIDS

CROSS-REFERENCE TO RELATED APPLICATIONS

This application is the 35 U.S.C. § 371 national stage of PCT application having serial number PCT/US2018/054550, filed on Oct. 5, 2018. This application also claims the benefit of and priority to U.S. Provisional Application Ser. No. 62/568,825, having the title "METHODS AND SYSTEMS OF HYPERPOLARIZATION OF A FLUID, METHODS OF USING HYPERPOLARIZED FLUID, AND METHODS AND SYSTEMS OF ADMINISTERING HYPERPOLARIZED FLUID", filed on Oct. 6, 2017; and to U.S. Provisional Application Ser. No. 62/721,655, having the title "METHODS AND SYSTEMS OF HYPERPOLARIZATION OF A FLUID, METHODS OF USING HYPERPOLARIZED FLUID, AND METHODS AND SYSTEMS OF ADMINISTERING HYPERPOLARIZED FLUID", filed on Aug. 23, 2018, the disclosures of which are incorporated herein by reference in their entireties.

STATEMENT REGARDING FEDERALLY SPONSORED RESEARCH OR DEVELOPMENT

This invention was made with Government support under CHE-1507230 awarded by the National Science Foundation. The Government has certain rights to this invention.

BACKGROUND

Magnetic resonance imaging (MRI) is an indispensable medical diagnostic tool that relies on the detection of nuclear magnetic resonance (NMR) transitions of proton magnetic moments of water in tissues. However, MRI is very inefficient in that only one water molecule out of about $10^6$ is effectively visible by MRI, which is one reason for the lengthy scanning times for patients. Thus, there is a need to overcome this deficiency.

SUMMARY

Embodiments of the present disclosure provide for methods and systems for making hyperpolarized fluids, methods and systems for introducing a hyperpolarized fluid to a subject, methods of imaging, methods of detecting protein-ligand interactions, and methods of enhancing the NMR signals of biopolymers having chemically exchangeable protons.

An embodiment of the present disclosure includes a method of making a hyperpolarized fluid, including exposing a fluid and parahydrogen to a catalyst. The method also includes making hyperpolarized fluid upon the interaction of the fluid, the parahydrogen, and the catalyst.

An embodiment of the present disclosure includes a method, which can include exposing a fluid and parahydrogen to a catalyst, making a hyperpolarized fluid upon the interaction of the fluid, the parahydrogen, and the catalyst, and introducing the hyperpolarized fluid to a subject.

An embodiment of the present disclosure includes a system for introducing a hyperpolarized fluid to a subject, which can include a holding vessel including a fluid and a catalyst. The system can further include a gas introduction system in communication with the holding vessel, wherein the gas introduction system is configured to introduce the parahydrogen into the holding vessel by bubbling the parahydrogen into the holding vessel, wherein the system is configured to expose the parahydrogen, the fluid, and a catalyst to one another to form the hyperpolarized fluid. The system can also include an intravenous system in fluidic communication with the holding vessel, wherein the intravenous system is configured to intravenously introduce the hyperpolarized fluid to the subject.

An embodiment of the present disclosure includes a system for making a hyperpolarized fluid, wherein the system can include a holding vessel and a gas introduction system in communication with the holding vessel. The gas introduction system can be configured to introduce a fluid-parahydrogen mixture to the holding vessel, wherein the fluid-parahydrogen mixture includes the parahydrogen dissolved in the fluid. The system can also include a catalyst introduction system in communication with the holding vessel, in which the catalyst introduction system is configured to introduce the catalyst to the holding vessel, and wherein the system is configured to expose the fluid-parahydrogen mixture and the catalyst to one another in the holding vessel to form the hyperpolarized fluid.

An embodiment of the present disclosure includes a system for making a hyperpolarized fluid, which can include a holding vessel including a catalyst. The system can also include a fluid vaporization system in communication with the holding vessel, wherein the fluid vaporization system is configured to introduce a vaporized fluid to the holding vessel. A gas introduction system in communication with the holding vessel can also be included, wherein the gas introduction system introduces parahydrogen into the holding vessel. The system can be configured to introduce the vaporized fluid and the parahydrogen to the catalyst to form the hyperpolarized fluid.

An embodiment of the present disclosure includes a method of imaging, including making a hyperpolarized fluid made using at least one of the forgoing methods, introducing the hyperpolarized fluid to a subject, wherein the hyperpolarized fluid is a contrast agent, and acquiring an image of subject using an imaging device.

An embodiment of the present disclosure includes a method of detecting protein-ligand interactions, including mixing a hyperpolarized fluid made from one of the foregoing methods with solution including a ligand and a protein, wherein there is a polarization transfer between the hyperpolarized fluid and the ligand. The method can also include measuring the protein-ligand binding by detecting a polarized ligand using gradient NMR spectroscopy.

An embodiment of the present disclosure includes a method of enhancing the NMR signals of biopolymers having chemically exchangeable protons including mixing a hyperpolarized fluid made from one of the foregoing methods with solution including the biopolymer, wherein there is a polarization transfer between the hyperpolarized fluid and the biomolecule mediated by proton exchange followed by a spin-spin coupling mediated polarization transfer to non-exchangeable nuclear spins of the biopolymer.

BRIEF DESCRIPTION OF THE DRAWINGS

Further aspects of the present disclosure will be more readily appreciated upon review of the detailed description of its various embodiments, described below, when taken in conjunction with the accompanying drawings. The components in the drawings are not necessarily to scale, emphasis instead being placed upon clearly illustrating the principles of the present disclosure.

FIGS. 1A-1D show example catalyst surface structures. (FIG. 1A) Bright-field TEM image of $Pt_3Sn$@$mSiO_2$ intermetallic nanoparticles (iNPs). (B) High-resolution HAADF STEM image of a $Pt_3Sn$ iNP taken along <111> zone axis. The brighter dots correspond to Pt atomic columns, while the darker sites correspond to Sn atomic columns, as shown by inset (size 2 nm 2 nm) in (FIG. 1B). (FIG. 1C) and (FIG. 1D) are structural models of Pt(111) and $Pt_3Sn$(111) surfaces, respectively (grey atoms are Pt). Red triangles in (C,D) identify three-fold Pt hollow sites.

(FIG. 2B) methanol-$d_4$ (CD3OD) at 105° C.; and (FIG. 2C) ethanol-$d_6$ ($CD_3CD_2OD$) at 105° C. Proton signals of the non-exchangeable methyl and methylene groups arise only from proton isotopic impurities in the per-deuterated neat liquids. In (C), * indicates a methanol impurity.

(FIG. 3A) Thermally polarized 400 MHz $^1H$ NMR spectra acquired after 0 through 5 $H_2$ bubbling cycles. The spectra were obtained after averaging of four free induction decays using a 120 s recycle delay. (FIG. 3B) Proton isotopic fraction (initially 0.2%, per manufacturer's specification), deduced from the hydroxy and methanol peak integrals in part A, plotted as a function of the number of bubbling cycles. (FIG. 3C) $^1H$ NMR spectra acquired at 9.4T immediately after 1 to 5 p-$H_2$ gas bubbling cycles. (FIG. 3D) $^1H$ SWAMP signal intensity as a function of p-$H_2$ gas bubbling cycles.

(FIG. 4A) Methanol-$d_4$, before and after a single $H_2$ bubbling cycle, showing a 30% increase in the —OH peak; and (FIG. 4B) ethanol-$d_6$ spectra before (bottom) and after (top) five $H_2$ bubbling cycles, with a 415% increase in the —OH peak. Only the —OH hydrogen signal increases after $H_2$ bubbling and not the non-exchangeable methyl and methylene proton in ethanol impurity peaks.

FIGS. 13A-C provide examples of the effect of bubbling of $H_2$ through a 1.8 mL $D_2O$ suspension of 50 mg $Pt_3Sn$@$mSiO_2$ on the 400 MHz $^1H$ NMR spectrum. (FIG. 13A) Spectra acquired at 9.4 T immediately after 1, 2 or 3 p-$H_2$ gas bubbling cycles. (FIG. 13B) Boltzmann thermally-polarized spectra acquired 120 s after acquisition of each of the spectra in part A using a recycle delay of 60s. (FIG. 13C) Proton isotopic fraction (initially 0.1%), calculated from the HDO peak integrals, as a function of the number of bubbling cycles. The tube was heated to 120° C. for 15 minutes, followed by 20 s bubbling of $H_2$ at 350 mL/min, and cooling to room temperature in a water bath for 10 minutes before loading into the NMR probe. Four free induction decays were averaged.

Figure 2A:
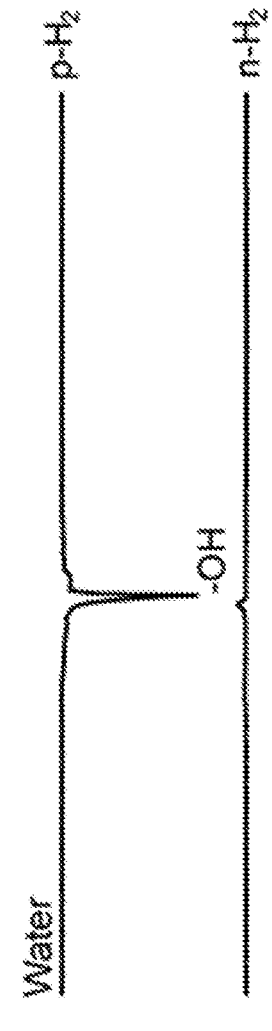
FIGS. 2A-2C are 9.4 T (400 MHz) liquid state $^1H$ NMR spectra acquired about 10 s after bubbling 7 bar of 50% para-enriched $H_2$ (i.e. p-$H_2$, upper spectra) or normal-$H_2$ (lower spectra) for 20 s at a flow rate of 350 mL/min through a suspension containing 50 mg $Pt_3Sn$@$mSiO_2$ and (FIG. 2A) water-$d_2$ ($D_2O$) at 120° C.

The drawings illustrate only example embodiments and are therefore not to be considered limiting of the scope described herein, as other equally effective embodiments are within the scope and spirit of this disclosure.

DETAILED DESCRIPTION

This disclosure is not limited to particular embodiments described, and as such may, of course, vary. The terminology used herein serves the purpose of describing particular embodiments only, and is not intended to be limiting, since the scope of the present disclosure will be limited only by the appended claims.

Where a range of values is provided, each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method may be carried out in the order of events recited or in any other order that is logically possible.

Embodiments of the present disclosure will employ, unless otherwise indicated, techniques of chemistry, biochemistry, microbiology, molecular biology, pharmacology, medicine, and the like, which are within the skill of the art. Such techniques are explained fully in the literature.

Prior to describing the various embodiments, the following definitions are provided and should be used unless otherwise indicated.

Unless otherwise defined, all technical and scientific terms used herein have the same meaning as commonly understood by one of ordinary skill in the art of microbiology, molecular biology, medicinal chemistry, physical chemistry, and/or organic chemistry. Although methods and materials similar or equivalent to those described herein can be used in the practice or testing of the present disclosure, suitable methods and materials are described herein.

As used in the specification and the appended claims, the singular forms "a," "an," and "the" may include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Definitions

By "administration" or "introduction" to a subject is meant to include introducing a hyperpolarized fluid or a solution including the hyperpolarized fluid of the present disclosure into a subject. The route of administration can include any route of administration, such as intravenous, oral, topical, subcutaneous, peritoneal, intraarterial, inhalation, vaginal, rectal, nasal, introduction into the cerebrospinal fluid, or instillation into body compartments can be used.

The term "an effective amount" are used interchangeably herein and refer to that amount of the hyperpolarized fluid being administered that is sufficient to affect the intended result. For example, an effective amount of the hyperpolarized fluid can include an amount used to achieve a desired image using for example a magnetic resonance imaging device. The effective amount may vary depending upon the intended application (in vitro or in vivo), or the subject, e.g., the weight and age of the subject, the manner of administration and the like, which can readily be determined by one of ordinary skill in the art. The specific dose will vary depending on the subject, the imaging device, desired goals, and the like. In an aspect, the dose of the hyperpolarized fluid may be administered either as a single bolus or continuously over the necessary period of time to achieve a desired image or series of images so as to trace the hyperpolarized fluid in the subject.

As used herein, the term "subject" includes humans, mammals (e.g., cats, dogs, horses, etc.), birds, and the like. Typical subjects to which embodiments of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. Additionally, for in vitro applications, such as in vitro diagnostic and research applications, body fluids and cell samples of the above subjects will be suitable for use, such as mammalian (particularly primate such as human) blood, urine, or tissue samples, or blood, urine, or tissue samples of the animals mentioned for veterinary applications. In some embodiments, a system includes a sample and a subject. The term "living subject" refers to the entire subject or organism and not just a part excised (e.g., a liver or other organ) from the living subject.

The term "polarization" refers to the difference in fractional population of the levels of a two-level system (for example, the spin-up and spin-down quantum states of the proton, denoted $|\uparrow\rangle$ and $|\downarrow\rangle$). Polarization of a two-level system is defined as:

$$P \equiv \frac{N_\uparrow - N_\downarrow}{N_\uparrow + N_\downarrow},$$

where $N_\downarrow$ and $N_\uparrow$ are the numbers of protons in the spin-up and spin-down states.

| ••••$|\downarrow\rangle$ ••••$|\uparrow\rangle$ | ⎯⎯⎯$|\downarrow\rangle$ ••••$|\uparrow\rangle$ | ••••$|\downarrow\rangle$ ⎯⎯⎯$|\uparrow\rangle$ |
|---|---|---|
| P = 0 Unpolarized | P = +1 Fully polarized | P = −1 Fully negatively polarized |

The term "hyperpolarization" refers to a non-thermal equilibrium nuclear spin polarization that is enhanced relative to the thermal equilibrium Boltzmann polarization.

The phrase "hyperpolarized fluid" refers to a liquid or gas containing molecules hosting hyperpolarized nuclear spins.

The term "parahydrogen" refers to the metastable spin isomer of dihydrogen with proton spins in a singlet state that is antisymmetric with respect to permutation of the two protons. For simplicity, the term parahydrogen will in some cases, depending on the context, also refer to dihydrogen gas that is only partially enriched in the parahydrogen spin isomer content relative to normal hydrogen, which is about 25% parahydrogen and about 75% orthohydrogen (the triplet state, which is symmetric with respect to permutation of the two protons).

Discussion:

Embodiments of the present disclosure provide for methods of making hyperpolarized fluid, systems for making hyperpolarized fluid, methods of introducing hyperpolarized fluid to a subject, systems of introducing hyperpolarized fluid to a subject, methods of imaging, systems of imaging, methods of tracing the flow and/or diffusion of the hyperpolarized fluid in the subject, detection of protein-ligand interactions, enhancement of the NMR signals of biomolecules with exchangeable protons (like proteins and nucleic acids), methods of probing dynamics of interfacial water, and the like.

An embodiment of the present disclosure includes methods of making a hyperpolarized fluid. In an aspect, the hyperpolarized fluid can be made by exposing a fluid (e.g., $H_2O$) and parahydrogen to a catalyst. The interaction of the fluid, the parahydrogen, and the catalyst produces the hyperpolarized fluid. The hyperpolarized fluid can be made in batch mode or in a continuous mode. Although not intending to be bound by theory, mechanisms for making the hyperpolarized fluid is discussed in the Example.

The method of making the hyperpolarized fluid can include multiple ways in which the fluid, the parahydrogen, and the catalyst are exposed to one another. In general, the components can be introduced to one another in sequence or simultaneously introduced to one another. In an aspect, the fluid molecule acquires one or more magnetized protons from parahydrogen by chemical exchange with no change in the molecular structure of the fluid. In another aspect, the fluid molecule acquires one or more of the hydrogen nuclei from parahydrogen, resulting in a chemical transformation of the molecular structure of the fluid. In an aspect, the sequence of introduction of these components can be varied to produce the hyperpolarized fluid. Additional details will be described herein and below.

In an aspect, embodiments of the present disclosure include a system for making the hyperpolarized fluid. In general, the system is configured to expose the parahydrogen, the fluid, and a catalyst to one another to form the hyperpolarized fluid. The system can include a temperature and pressure controlled mixing vessel connected to a holding vessel and a gas introduction system in communication with the holding vessel. In an aspect, the holding vessel can include a fluid and/or a catalyst. The gas introduction system can be configured to introduce gases (e.g., the parahydrogen) or vapors (e.g., vaporized fluid) into the holding vessel.

In an aspect, the holding vessel can include a volume where the hyperpolarized fluid that can be produced at an elevated pressure (e.g., about 1 to 100 bar) and temperature (e.g., about 25° Celsius to 300° Celsius) and optionally a separate area where the hyperpolarized fluid can be stored prior to use (e.g., in an intravenous system). The holding vessel can include one or more inlets and outlets for the components. The holding vessel can be of dimensions to include an appropriate amount of the components and the produced hyperpolarized fluid. The holding vessel can be made of a material such as stainless steel, aluminum, plastic, glass, quartz, or a combination thereof. For example, the vessel in which the hyperpolarized fluid is produced by interaction could include a heavy-wall syringe body fitted with a sealed piston. The vessel is constructed in such a manner to be safely pressurized and heated to optimize the production of the hyperpolarized fluid, depending on the fluid, catalyst composition and properties. The outlet of the syringe is fitted with an appropriate filter element or separation system that prevents the catalyst from being discharged with the fluid once it has been hyperpolarized. Alternatively, the syringe could serve as the storage vessel and intravenous delivery device that is charged with hyperpolarized fluid produced in a separate heated, pressurized vessel.

The gas introduction system can include appropriate equipment to acquire (if part of a different system) and/or flow the gas (e.g., parahydrogen) and/or vapor to the holding vessel. For example, the gas introduction system can include tubing or catheter, flow valves, pressure gauges, syringe pumps, thermocouples, flow meters, and the like to control introduction into the holding vessel through the inlet valve.

In each of the methods and systems for making the hyperpolarized fluid, after the hyperpolarized fluid is made, the hyperpolarized fluid can be frozen, condensed or deposited to form hyperpolarized solid. In an aspect, when the hyperpolarized fluid is in the vapor phase, a cryogenic system can be used to condense the hyperpolarized fluid as a hyperpolarized solid. In the solid state, molecular motion is quenched, and the nuclear spin relaxation lifetime of protons and other nuclei can be prolonged. This allows the hyperpolarized fluid vapors to be accumulated by deposition as a solid by passing the gas stream through a cold finger or cold trap cooled to a cryogenic temperature (e.g., 77 K) and stored for much longer time periods than in the gas or liquid phases. In an aspect, to increase the lifetime of the hyperpolarized spin state, a magnetic field may be applied to the cryogenic holding vessel.

Now having described the methods and systems generally, additional details regarding the methods and systems are provided.

In an aspect, the fluid can be a gas or a liquid. In an aspect, the fluid can be one including —OH containing molecules, molecules including an amide or an amino group, an amino acid, a sugar, a carboxylic acid, a combination thereof, or any other moiety with an exchangeable proton. The —OH containing molecule can include: water, an alcohol (e.g., methanol, ethanol, propanol), or a combination thereof. The molecules with an amide or an amino group can include: methylamine, ammonia, ethaneamide, methanamide, or a combination thereof. The amino acid can include any one of the known amino acids including the known twenty amino acids in particular, glycine, alanine, valine, serine, threonine, asparagine, glutamine, cysteine, or a combination thereof. The sugar can include glucose, for example. The carboxylic acid can include acetic acid, carbonic acid, propionic acid, oxalic acid, benzoic acid, formic acid, aspartic acid, glutamic acid, or a combination thereof. In an aspect, the fluid can be $O_2$, as a pure gas, in a mixture with p-$H_2$ and an inert carrier gas (e.g., $N_2$), in a gaseous or dissolved phase.

In an aspect, the catalyst is insoluble or substantially insoluble in the fluid. In general, the substantially insoluble catalysts can include catalysts that are soluble to a level that the metals are present in an amount that it is not harmful to the subject to which the hyperpolarized fluid is administered. For example, Table 1 reports the Pt and Sn concentrations that leached into the supernatant ($D_2O$) from an aqueous slurry of the $Pt_3Sn@mSiO_2$, analyzed by ICP-MS on different isotopes, which shows that the catalyst is substantially insoluble.

TABLE 1

Concentration of Pt and Sn that was Leached into the Supernatant from Pt$_3$Sn@mSiO$_2$ Analyzed by ICP-MS on Different Isotopes (from Ref. 16 in the Example)

| Sample | $^{118}$Sn (ppb) | $^{120}$Sn (ppb) | $^{194}$Pt (ppb) | $^{195}$Pt (ppb) | $^{196}$Pt (ppb) |
|---|---|---|---|---|---|
| Pt$_3$Sn@mSiO$_2$ | 69.62 ± 0.20 | 69.93 ± 0.23 | 13.05 ± 0.16 | 12.49 ± 0.30 | 14.67 ± 0.06 |

In an embodiment, the catalyst can be a Group VIII, IB, or IIB transition metal based catalyst including at least two different metals (e.g., a bimetallic catalyst). In an aspect, the catalyst can include a one or more of the following: Pt, Pd, Cu, Au, Ag, Rh, Ru, Ir, Ni, Sn, Co, Zn, Ce, Ti, Al, Fe, Si or O. In an embodiment, at least two of the following are included in the catalyst: Pt, Pd, Cu, Au, Ag, Rh, Ru, or Ir. In particular, the catalyst can be one or more of the following: PtPd, PtBi, PtZn, Pt$_3$Zn, PtRu, PtRh, PtPb, Pt$_3$Co, Pt$_3$Ti, Pt$_3$V, Pt$_3$Ni, PtAu, PtFe, PtCu, PtGe, PtIr, PdCu, AuCu, CuFe, FeMnCu, CuNi, CuRu, CuCo, CuAg, AuPd, PdNi, PdFe, PdRu, PdSn, PdBi, PdPb, AgPd, PdCo, PdMn, PdIr, RhCo, RhAg, RhFe, RhGe, RhNi, RhRe, RhSn, RuCo, RuSn, RuAg, NiRu, RuCr, IrNi, CoIr, or AuAg, In an aspect, the catalyst can be coated (e.g. having a porous coating to protect the catalyst but still allowing the fluid to access the surface) or uncoated. In an embodiment, the catalyst can be a particle such as a nanoparticle (e.g., at least one dimension of about 0.1 to 1000 nm) or microparticle (e.g., at least one dimension or about 1 to 1000 μm) that is spherical or nonspherical. In an aspect, the catalyst can be a core shell particle (e.g., nanoparticle) having a Pt$_3$Sn core or other bimetallic composition and a mesoporous silica shell. In an aspect, the catalyst can include isolated atoms, clusters, or particles, on a support material, which can include: single-wall or multi-wall carbon nanotubes, a metal oxide, including silica, titanium oxide, cerium oxide, aluminum oxide, or tin oxide.

The amount of catalyst should be sufficient to provide enough adsorption sites to accommodate both parahydrogen and sufficient number of fluid molecules. Ideally, the total number of surface adsorption sites of the catalyst should be sufficient to allow all molecules in the fluid volume contained in the vessel to exchange between the bulk fluid and surface adsorbed phases as many times as is required for each fluid molecule to acquire hyperpolarization either by exchange of one or more magnetized protons from adsorbed parahydrogen during a period less than the nuclear spin relaxation time on the fluid molecules or via a mechanism involving the coherent and/or incoherent spin-spin coupling mediated hyperpolarization transfer from parahydrogen to the fluid molecule, as described in the Example. In the Example, 50 mg of Pt$_3$Sn@mSiO$_2$ catalyst in 1.8 mL of D$_2$O was used. The amount of catalyst required will depend on the particle size, as the surface to volume ratio scales as 1/R, where R is the particle radius (assuming a spherical particle shape), the surface composition, and the rate of exchange between the surface and the bulk water, as well as the type of catalyst.

In an aspect, the fluid can be diluted in an aprotic solvent. The aprotic solvent can include: dioxane, nitromethane, acetonitrile, acetone, dichloromethane, or a combination thereof. In an aspect, the aprotic solvent can be a perdeuterated and partially deuterated form of each of the solvents listed above or herein. In an embodiment, the fluid is water and is diluted in the aprotic solvent.

Now having described some embodiments of the present disclosure, additional embodiments and details are provided below.

In an embodiment, the method includes mixing the fluid with the catalyst to produce a fluid-catalyst mixture, emulsion, or suspension. Subsequently, the parahydrogen can be introduced to the fluid-catalyst mixture by bubbling the parahydrogen through the fluid-catalyst mixture, or by other effective method for gas dissolution, including aspiration, cavitation, elutriation or sonication. Once the hyperpolarized fluid is formed, the catalyst can be easily removed from the hyperpolarized fluid. The catalyst can be separated from the hyperpolarized fluid using an appropriate filter or centrifugation.

In an aspect, embodiments of the present disclosure include a system for making the hyperpolarized fluid. In general, the system is configured to expose the parahydrogen to the fluid and the catalyst by bubbling the parahydrogen so it passes through the fluid to form the hyperpolarized fluid. In an aspect, the solubility of the parahydrogen in the fluid can be increased by elevating the pressure of the mixing chamber. The holding vessel and the gas introduction system are similar to those described above. The holding vessel and/or the gas introduction are configured to control the bubble size and rate of the bubbles produced to pass through the fluid. The holding vessel can be configured with a device for acoustic cavitation to increase the rate of mixing and dissolution of the gas into the liquid. The holding vessel is configured so that the hyperpolarized fluid and the catalyst can be quickly separated in a manner that limits the spin relaxation losses of the hyperpolarized fluid. In an aspect, the holding vessel may include a separate chamber to hold the hyperpolarized fluid that has been separated from the catalyst.

In another embodiment, the method of making the hyperpolarized fluid includes dissolving the parahydrogen with the fluid to form a fluid-parahydrogen mixture. The parahydrogen can be pre-dissolved in the fluid by diffusion across a suitable gas-dissolution membrane separating the gas and liquid. Subsequently, the catalyst and the fluid-parahydrogen mixture can be exposed to one another. For example, the fluid-parahydrogen mixture can be flowed across or through the catalyst (e.g., a catalyst bed).

In an aspect, a system for making the hyperpolarized fluid by dissolving the parahydrogen with the fluid is provided. In this embodiment, the fluid and the parahydrogen are mixed prior to being exposed to the catalyst. The parahydrogen is dissolved in the fluid and is referred to as a fluid-parahydrogen mixture. In general, the system to make the hyperpolarized fluid is configured to expose the fluid-parahydrogen mixture and the catalyst to one another in the holding vessel to form the hyperpolarized fluid. In one aspect, the holding vessel can be used to mix the fluid and the parahydrogen. In another aspect, the gas introduction system can be configured to mix the parahydrogen and the fluid to dissolve the parahydrogen in the fluid. In another aspect, the fluid-parahydrogen mixture can be made separately from the gas introduction system or holding vessel. The catalyst can be added to the holding vessel before or after the formation of the fluid-parahydrogen mixture.

In an aspect, the method of forming the hyperpolarized fluid includes exposing the vaporized fluid and parahydrogen to the catalyst to form a vaporized hyperpolarized fluid. The fluid can be vaporized using known techniques. The vaporized fluid and the parahydrogen can be mixed prior to exposure to the catalyst. In an aspect, the vaporized fluid and the parahydrogen can be flowed across the catalyst to from the hyperpolarized fluid.

In an aspect, the fluid is oxygen. The surface of the bimetallic catalyst (e.g., $Pt_3Sn$, $Pd_3Sn$) catalyzes the hydrogenation of oxygen. The parahydrogen is reacted with the oxygenated surface, either simultaneously in a mixture of p-$H_2$ or $O_2$, or sequentially, where the catalyst is initially saturated with oxygen prior to admission of p-$H_2$. The co-adsorbed parahydrogen and oxygen react to form hyperpolarized water, which desorbs from the surface is collected by one of the methods described below. The net reaction is:

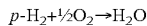

$$p\text{-}H_2 + \tfrac{1}{2}O_2 \rightarrow H_2O$$

The hydrogenation of oxygen resulting in hyperpolarized water may occur by either pairwise or non-pairwise addition. In the latter case, hyperpolarization of the water molecule via transfer of only a single proton from the parahydrogen molecule necessarily involves a One H-PHIP like mechanism, as described in the Example. The reaction of parahydrogen with oxygen may be carried out by allowing the gases to interact on the solid catalyst, or it could be mediated in a solution containing dissolved parahydrogen and oxygen and suspended catalyst particles. In an aspect, the solid 'catalyst" material is an oxygen bearing oxide material such as cerium oxide ($CeO_2$) that generates hyperpolarized water when reacted with parahydrogen. The efficiency of this process may be enhanced by deposition of a metal like In, Pt, or Pd in the form of single atoms, pairs of closely spaced metal atoms, clusters or nanoparticles.

In an embodiment, the system for making the hyperpolarized fluid can include a holding vessel including a catalyst, a fluid vaporization system in communication with the holding vessel, and a gas introduction system in communication with the holding vessel. The system for making the hyperpolarized fluid is configured to introduce the vaporized fluid and the parahydrogen to the catalyst to form the hyperpolarized fluid. The holding vessel is similar to that described herein. The gas introduction system introduces parahydrogen into the holding vessel and is similar to those described herein. The fluid vaporization system is configured to introduce a vaporized fluid to the holding vessel. The fluid vaporization system includes heating elements to vaporize the fluid and other elements to control the flow of the vaporized fluid into the holding vessel.

Now having described methods and systems of making hyperpolarized fluid, other aspects of the present disclosure are presented. An aspect of the present disclosure includes methods and systems for administering the hyperpolarized fluid to a subject (e.g., a human). In an aspect, the hyperpolarized fluid can be used as a contrast agent. During the administration and/or after administration the subject can be imaged using a magnetic resonance imaging system.

In an aspect, the hyperpolarized fluid can be introduced to a subject. In an embodiment, the method includes exposing a fluid and parahydrogen to a catalyst to form the hyperpolarized fluid according to any of the methods and systems provided herein. After the hyperpolarized fluid is produced, the hyperpolarized fluid can be introduced to the subject. For example, the hyperpolarized fluid to the subject intravenously. In an aspect, the hyperpolarized fluid can be mixed with a saline solution.

In an aspect, embodiments of the present disclosure include a system for introducing (e.g., administering an effective amount) the hyperpolarized fluid to a subject. The system can include a holding vessel, a gas introduction system in communication with the holding vessel, and an intravenous system in fluidic communication with the holding vessel. In an aspect, the holding vessel can include a fluid and a catalyst. In an aspect, the gas introduction system can be configured to introduce the parahydrogen into the holding vessel (e.g., by bubbling the parahydrogen into the holding vessel), where the system is configured to expose the parahydrogen, the fluid, and a catalyst to one another to form the hyperpolarized fluid. Any of the other methods for making the hyperpolarized fluid can also be used to produce the hyperpolarized fluid. The intravenous system is configured to intravenously introduce the hyperpolarized fluid to the subject. The intravenous system includes a pump, flow regulator, tubing or catheter, and the like to facilitate the flow of the hyperpolarized fluid into the subject. In an aspect, the intravenous system includes a set up to mix the hyperpolarized fluid with a solution that is introduced to the subject via one or more syringes, for example the solution can be a saline solution, or the fluid that is hyperpolarized consists of a saline solution. The intravenous system can include other components as are typically used in intravenous administration of a contrast agent.

Once the hyperpolarized fluid is introduced to the subject, an image of the subject (or a portion of the subject) can be acquired using an imaging device. In an embodiment, the imaging device can be a magnetic field resonance device. In an embodiment, the magnetic field resonance device can be a low field or ultra-low field magnetic resonance device. In an embodiment, the magnetic field resonance device can be a fast or super-fast magnetic resonance device.

In an aspect, the hyperpolarized fluid can be used in a spectrometer or imaging system that utilizes SQUID (superconducting quantum interference device) detectors, which measures magnetic flux directly rather than its derivative, as in the conventional NMR and MRI based on Faraday's law. SQUID detection is well suited for MRI at ultra-low magnetic fields. The hyperpolarized fluid of the present disclosure can be used in SQUID detected ultra-low field MRI.

In an embodiment, the hyperpolarized fluid can be introduced into an organ and images can be acquired by tracking the perfusion trajectory of the hyperpolarized fluid in the organ (e.g., heart).

In an embodiment, the present disclosure includes methods of detecting protein-ligand interactions. The method can include mixing the hyperpolarized fluid made from any one of the methods provided herein with solution including a ligand and a protein. Upon mixing, there is a polarization transfer between the hyperpolarized fluid and the ligand to form a polarized ligand, which can be measured. In this regard, the protein-ligand binding can be measured by detecting a polarized ligand using NMR spectroscopy. The measured signal of the polarized ligand can be enhanced via the polarization transfer from hyperpolarized proton to the ligand proton. The evidence of ligand binding is indicated by the sign of the signal enhancement. Polarization transfer between the hyperpolarized fluid and the ligand occurs via an intermolecular nuclear Overhauser effect (NOE). Rapidly tumbling free ligands exhibit a negative NOE signal enhancement, while slowly tumbling ligand-protein complexes acquire positive NOE enhancement.

In an aspect of the present disclosure, the catalyst can be used to convert the parahydrogen spin order into a singlet-triplet imbalance (STI) on the fluid. In an aspect, the proton exchangeable fluid is diluted in one of the following aprotic solvents: dioxane, nitromethane, acetonitrile, acetone, dichloromethane, thereby slowing the rate of intermolecular proton exchange, which can extend the lifetime of STI on the fluid molecules. In an embodiment, an STI can be induced on $H_2O$ molecules in the vapor phase or in a dilute solution in an aprotic solvent. The STI can be prepared in batch mode by bubbling hydrogen through the catalyst suspension or in a continuous-flow mode by passing the fluid containing dissolved $p-H_2$ through a catalyst reactor bed. Acoustic cavitation can be applied to increase the rate and efficiency of dissolution of hydrogen into the solution. In an aspect, the lifetime of the STI of the fluid molecules can be prolonged by deposition or freezing as a solid at cryogenic temperatures. Deposition or freezing also provides a means for the accumulation and storage of fluid molecules with the STI.

While embodiments of the present disclosure are described in connection with the Examples and the corresponding text and figures, there is no intent to limit the disclosure to the embodiments in these descriptions. On the contrary, the intent is to cover all alternatives, modifications, and equivalents included within the spirit and scope of embodiments of the present disclosure.

Example 1

Brief Introduction to Example 1

This example describes the discovery that $Pt_3Sn$ intermetallic nanoparticles (iNPs), synthesized within a protective mesoporous silica shell ($Pt_3Sn@mSiO_2$), catalyze alignment of the proton magnetic moments in water as well as methanol and ethanol molecules using parahydrogen. In this SWAMP effect (Surface Waters Are Magnetized by Parahydrogen), a negative proton spin temperature is induced simply by bubbling parahydrogen through a suspension of the iNP catalyst in the neat liquid. The polarization transfer is mediated by symmetry-breaking surface interactions on $Pt_3Sn@mSiO_2$ nanoparticles. The hallmark of SWAMP is intense stimulated emission NMR signals of the exchangeable hydroxy protons. Non-exchangeable methyl or methylene protons also become hyperpolarized, an observation that provides insight into the molecular mechanism for polarization transfer. SWAMP has a myriad of potential applications, ranging from low-field MRI to drug discovery.

Discussion of Example 1

When the 1932 Nobel Prize in Physics was awarded to Heisenberg "for the creation of quantum mechanics," it was said to have led, inter alia, to the discovery of the allotropic forms of hydrogen. The allotropes are parahydrogen ($p-H_2$) and orthohydrogen ($o-H_2$), differing in the relative orientation of their proton spins. The symmetric ($I=1$, $o-H_2$) and antisymmetric ($I=0$, $p-H_2$) spin functions are associated with antisymmetric and symmetric rotational states, respectively, in accordance with the Pauli Principle. Owing to the large rotational splitting of the homonuclear diatomic molecule, a significant para-enrichment of 50% $p-H_2$ ($x_p=0.5$) can be achieved even at 77 K, while a near pure singlet-state with $x_p=0.97$ is obtained at 30 K. After thermal equilibration over an ortho/para conversion catalyst and warming to room temperature, the metastable singlet-triplet imbalance (STI) can persist in the gas for months.

The $H_2O$ molecule also exists in ortho ($o-H_2O$) and para ($p-H_2O$) forms, but unlike $H_2$, the preparation of the pure $H_2O$ spin isomers is not so easily achieved.[1,2] The separation of $o-H_2O$ and $p-H_2O$ by column chromatography was claimed[3] but later disputed in the literature.[4] One might speculate that $p-H_2O$ could be prepared from $D_2O$ by Pairwise Replacement Catalysis (PRC), as shown in scheme 1, where a pair of protons (or deuterons) in a random spin state on a molecule is replaced by a pair of protons in a singlet state.[5] Unfortunately, the singlet spin order would be rapidly (c.a. 1 ms) randomized by proton exchange in liquid $H_2O$ or $D_2O$.[6,7] Scheme 1A depicts the creation of non-equilibrium proton Zeeman order (i.e. hyperpolarization) by chemical exchange of a single hydrogen from $p-H_2$. While this scheme produces hyperpolarized water in a form that is robust to proton exchange, it implies a preferential transfer of a proton in a specific spin state (e.g. $|\alpha\rangle$ or $|\beta\rangle$), which would appear to violate the particle indistinguishability in the system of two identical Fermions.

Scheme 1

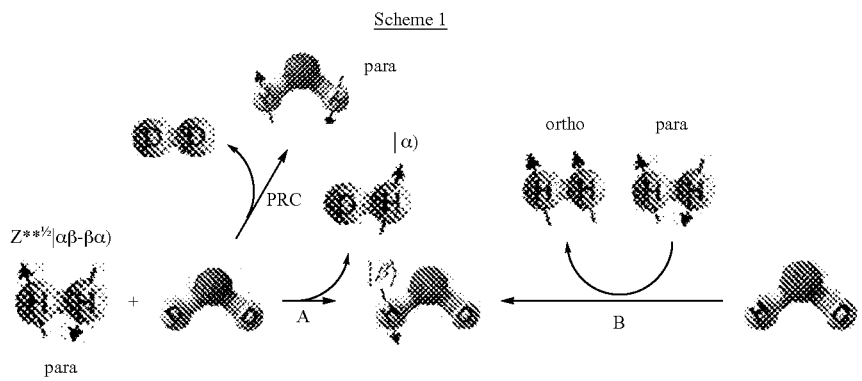

Scheme 1B depicts the production of hyperpolarized HDO via intermolecular spin exchange between (initially unpolarized) HDO and p-$H_2$, yet it too, as presented, is inconsistent with the Born interpretation of the singlet spin function. Here we show that the quantum paradox implicit to schemes 1A or 1B can be finessed by symmetry breaking surface interactions in co-adsorbed p-$H_2$ and water or alcohols. In a heterogeneous process referred to as the SWAMP effect (Surface Waters Are Magnetized by Parahydrogen), hyperpolarized water, methanol and ethanol is produced using p-$H_2$. The alignment of the protons in the neat liquids is catalyzed on the surface of insoluble $Pt_3Sn@mSiO_2$ intermetallic nanoparticles (iNPs) encapsulated in mesoporous silica,[8,9] with a surface structure shown in FIGS. 1A-1D.

In the late 1980's, the PASADENA effect (Parahydrogen And Synthesis Allows Dramatically Enhanced Nuclear Alignment) was introduced, where the hidden nuclear spin order of p-$H_2$ is revealed by symmetry-breaking hydrogenation chemistry.[10,11] In theory, the room-temperature parahydrogen-induced polarization (PHIP) enhanced NMR signals can exceed those derived from the high-field thermal equilibrium Boltzmann spin polarization by five orders of magnitude. Over the years, multiple variants of the PASADENA effect have been developed and demonstrated on scores of different substrates, enabling molecular magnetic resonance imaging (MRI) and catalysis studies.[12-20] Despite three decades of intensive research, the exciting first report of PHIP-hyperpolarized water was published only a few months ago.[21] They used homogeneous $D_2O/H_2O$ solutions containing a dissolved [Ir(Cl)(IDEG)(COD)] complex and a L-histidine additive. The relationship of this observation to the SWAMP effect is considered below.

An intrinsic advantage of PHIP by heterogeneous catalysis is that the pure hyperpolarized fluid can be quickly and completely separated from the catalyst,[22] allowing the catalyst to be re-used. This is crucial for prospective biomedical applications of hyperpolarized water due to its relatively short proton spin relaxation time.

Results

In the SWAMP experiment, a negative spin temperature is induced simply by bubbling p-$H_2$ gas through a heterogeneous suspension containing only the insoluble $Pt_3Sn@mSiO_2$ iNP catalyst and the neat liquid. The resulting stimulated emission NMR signal of the hydroxy protons can be seen in FIG. 2. Non-exchangeable methyl and methylene protons of methanol and ethanol, respectively, are also hyperpolarized, an observation which must be accounted for in any mechanistic hypothesis. $Pt@mSiO_2$ and $PtSn@mSiO_2$ catalysts[22] were also synthesized and tested, but did not yield SWAMP signals. TEM images of $Pt_3Sn@mSiO_2$ and model surfaces of Pt(111) and $Pt_3Sn$ (111) are shown in FIGS. 1A-1D. The alternating contrast of different atomic columns seen in the image in FIG. 1B is due to chemical ordering in the $Pt_3Sn$ particle.

The surface-science literature on Pt and Pt—Sn alloys provides insights into the surface interactions that may play a role in mediating the conversion of parahydrogen spin order into observable magnetization of water and alcohols. Hydrogen adsorption and diffusion on Pt and Pt—Sn alloys has been studied both theoretically[23] and experimentally.[24,25] Facile dissociative adsorption of $H_2$ occurs on three-fold Pt (111) sites. As illustrated in FIGS. 1C, 1D, monometallic Pt(111) bears contiguous three-fold hcp (hexagonal close-packed) and fcc (face-centered cubic) Pt sites (vertex and base connected), while the $Pt_3Sn(111)$ surface bears only isolated three-fold Pt sites (vertex connected). In our previous work, $PtSn@mSiO_2$ was found to yield the highest pairwise selectivity (11%) in the hydrogenation of propene with p-$H_2$,[22] attributed to the absence of the three-fold Pt surface sites and restriction of diffusion on this catalyst. On the $Pt_3Sn(111)$ surface, the presence of both Sn and three-fold Pt sites on the catalyst surface appears to be crucial to the SWAMP activity.

Figure 2B:
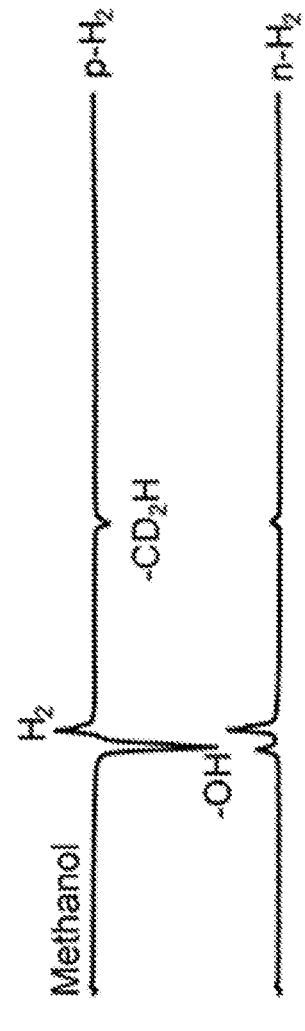
Figure 2C:
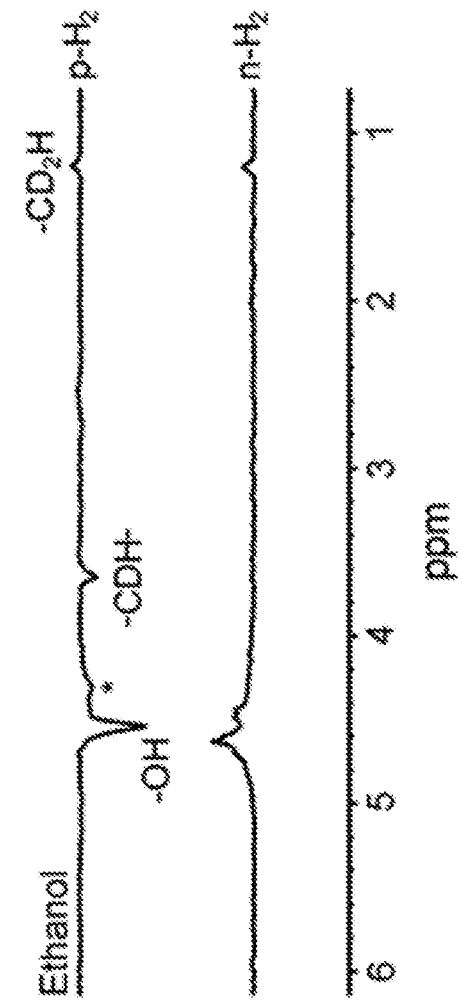

Experiments were performed on suspensions of 50 mg of the insoluble catalyst solids and 1.8 mL of liquid $D_2O$, $CD_3OD$, or $CD_3CD_2OD$ in a 10 mm NMR tube fitted with a PEEK cap. Capillary tubing feed-throughs in the cap allowed controlled bubbling and venting of the gases. FIG. 2A presents the spectrum obtained with $D_2O$ (99.9% D, 99.5% chemical purity). The NMR tube was pressurized to 7 bar and heated to 120° C. in the earth's magnetic field and p-$H_2$ was bubbled through the liquid suspension for about 20 s. The sample was then rapidly transferred by hand (in about 10s) from the lab bench to the field center of the 9.4 T NMR spectrometer where the $^1H$ NMR spectrum was immediately acquired. The intense emission phase HDO resonance can be seen in the upper spectrum of FIG. 2A. The lower spectrum, obtained after repeating the same experiment with n-$H_2$, exhibits only a small absorption phase peak that is attributed to incompletely thermally polarized water protons. Experiments with neat methanol-$d_4$[26] and ethanol-$d_6$[27] exhibited similar hydroxy proton emission signals (upper spectra in FIG. 2B and FIG. 2C). In methanol, the methyl (—$CHD_2$) protons also exhibited hyperpolarization. Note that the thermally polarized —OH signal is also larger than the thermally polarized methyl peak, reflecting different proton isotopic fractions at the two sites. For ethanol, both the hydroxy and methylene (—CHD-) protons display stimulated emission signals, while the methyl proton signal appears unaffected.

Figure 3B:
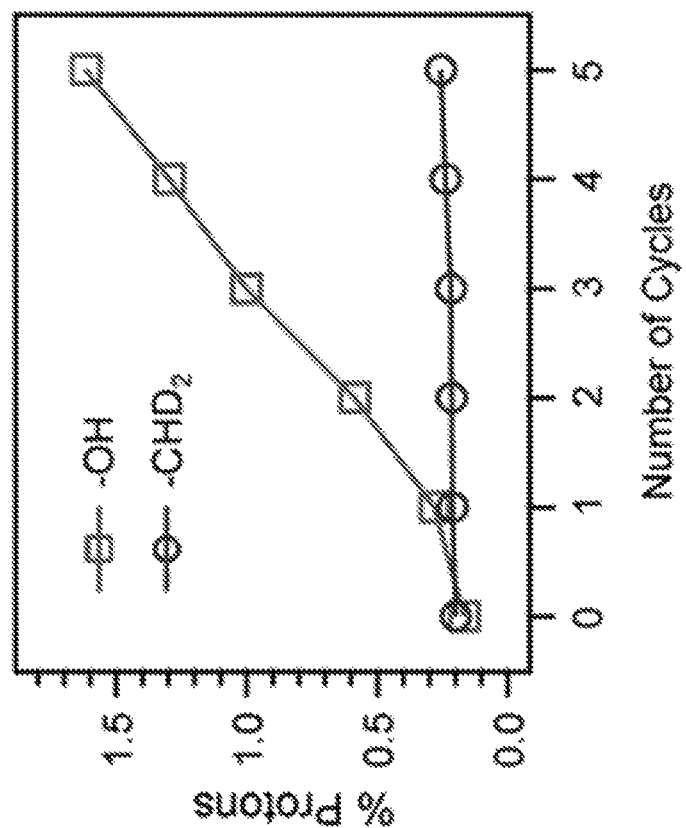
FIGS. 3A-3D illustrate the effect of the amount of bubbling of $H_2$ through suspensions of 50 mg $Pt_3Sn$@$mSiO_2$ in methanol-$d_4$, initially with 99.8% deuterium isotopic purity.
Figure 3A:
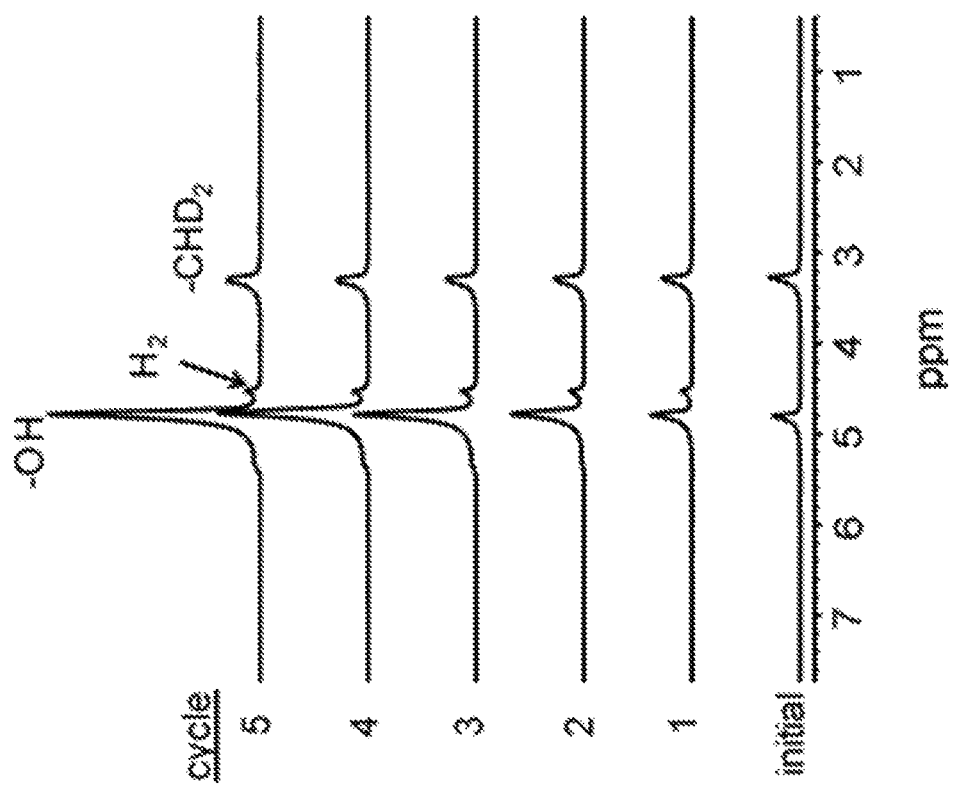
Figure 3D:
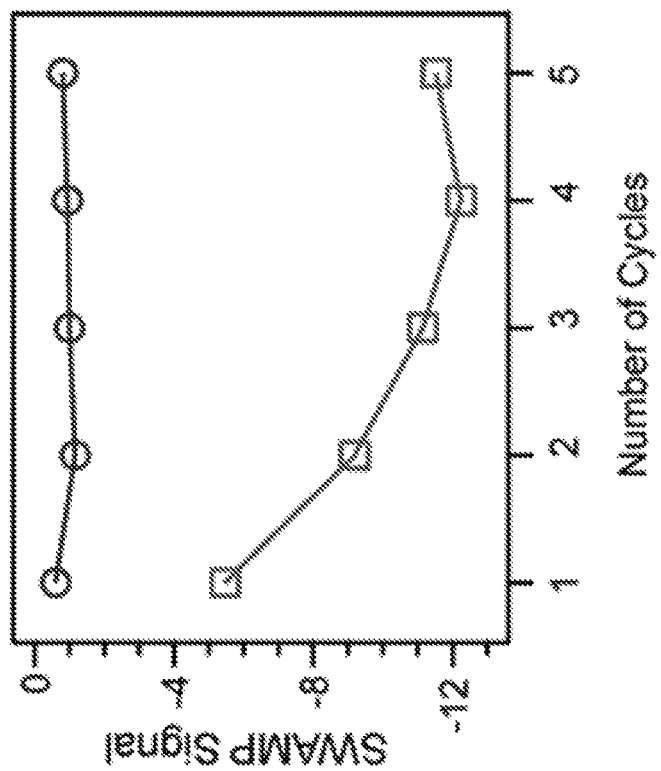

The thermally polarized spectra presented in FIG. 3A were acquired at Boltzmann equilibrium following 0 to 5 cycles of $H_2$ bubbling, where a cycle consists of heating the tube to 105° C. for 15 minutes, bubbling of $H_2$ for 20 s at 350 mL/min, and cooling to room temperature in a water bath for 10 minutes before loading into the NMR probe. The methanol —OH signals are seen to increase linearly (after the first cycle) with the total amount of $H_2$ bubbled through the liquid, corresponding to a rise in the proton isotope fraction from 0.2% (manufacturer's specification) to 1.6% (FIG. 3B). A similar rise of the —OH peak with isotope fraction was observed in experiments with $D_2O$ (see FIG. 13B, 13C). The increase can only be explained by H/D exchange of a proton in $H_2$ with a deuteron in —OD (i.e. $H_2+CD_3OD→HD+CD_3OH$). In contrast, the peak of the non-exchangeable methyl protons did not significantly change.

Figure 4A:
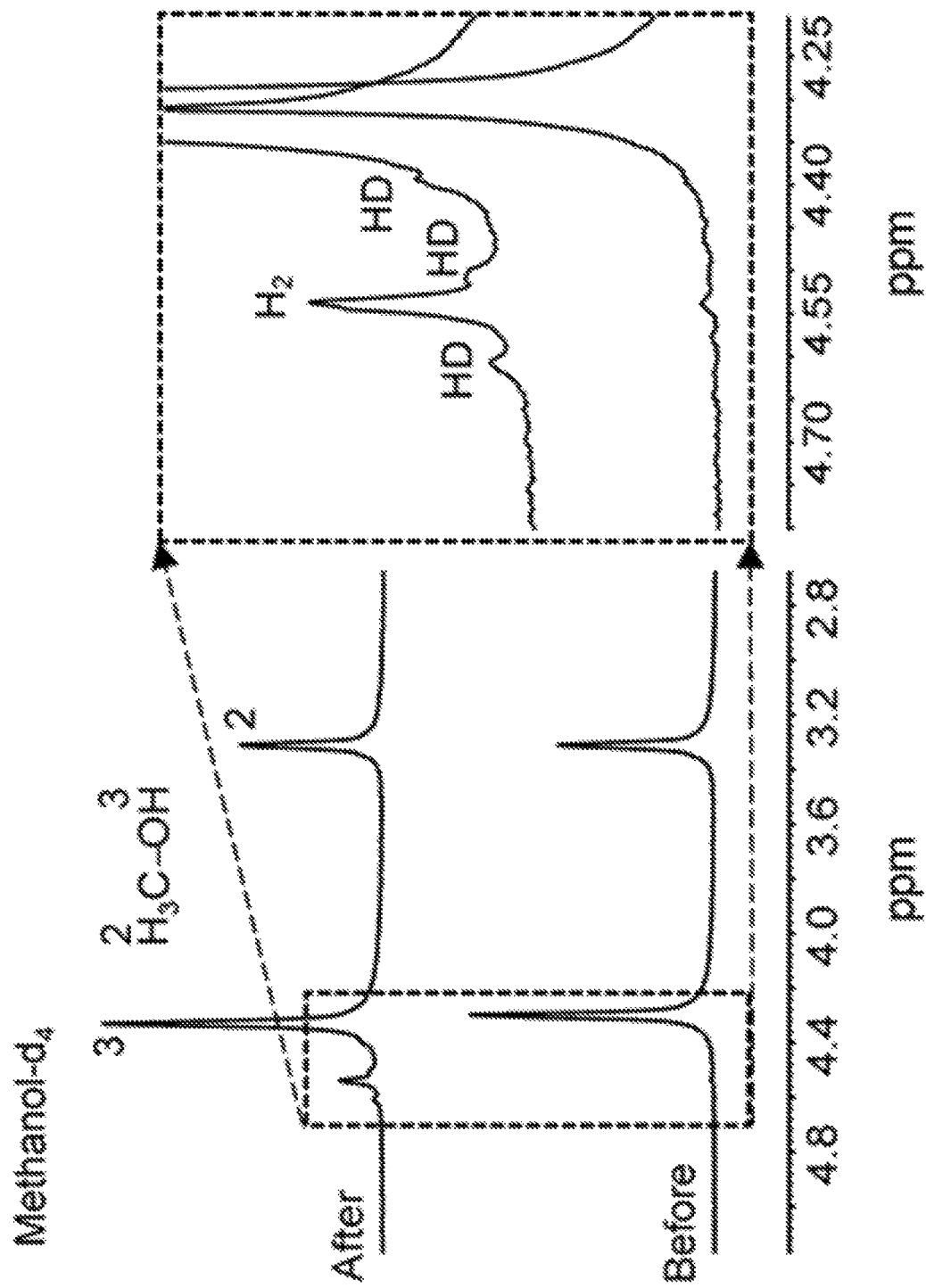
FIGS. 4A-4B are conventional, fully relaxed, 9.4T Boltzmann polarized $^1H$ NMR spectra exhibiting H-D exchange, in suspensions containing $Pt_3Sn$@$mSiO_2$ at 105° C.
Figure 4B:
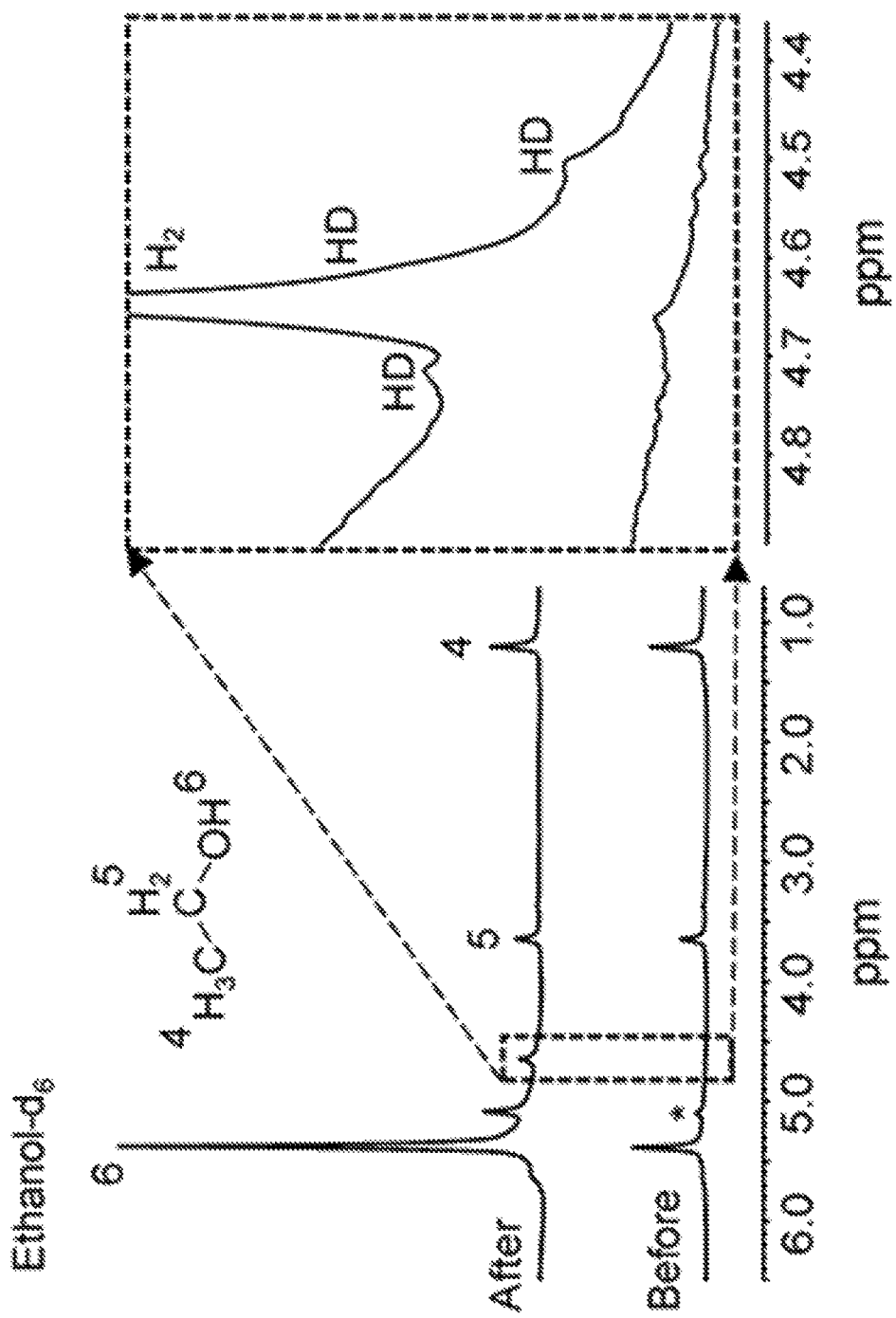

Evidence for H/D exchange in the $CD_3OD$ and $CD_3CD_2OD$ samples can be seen in the Boltzmann-polarized $^1H$ spectra recorded before and after bubbling in FIG. 4. Note that prior to any $H_2$ bubbling through the ethanol-$d_6$ sample (FIG. 4B), the thermally polarized peaks of the exchangeable (i.e. —OH) and non-exchangeable protons are comparable, but only the —OH peak has grown larger after $H_2$ bubbling. H/D exchange is further confirmed by the observation of a dissolved 1:1:1 HD triplet with a 42.9 Hz $^1J_{HD}$ coupling constant,[19,28,29] as seen in the expanded views in FIG. 4A, B. The deuterons in HD can only originate from methanol-$d_4$ or ethanol-$d_6$ molecules.

Figure 3C:
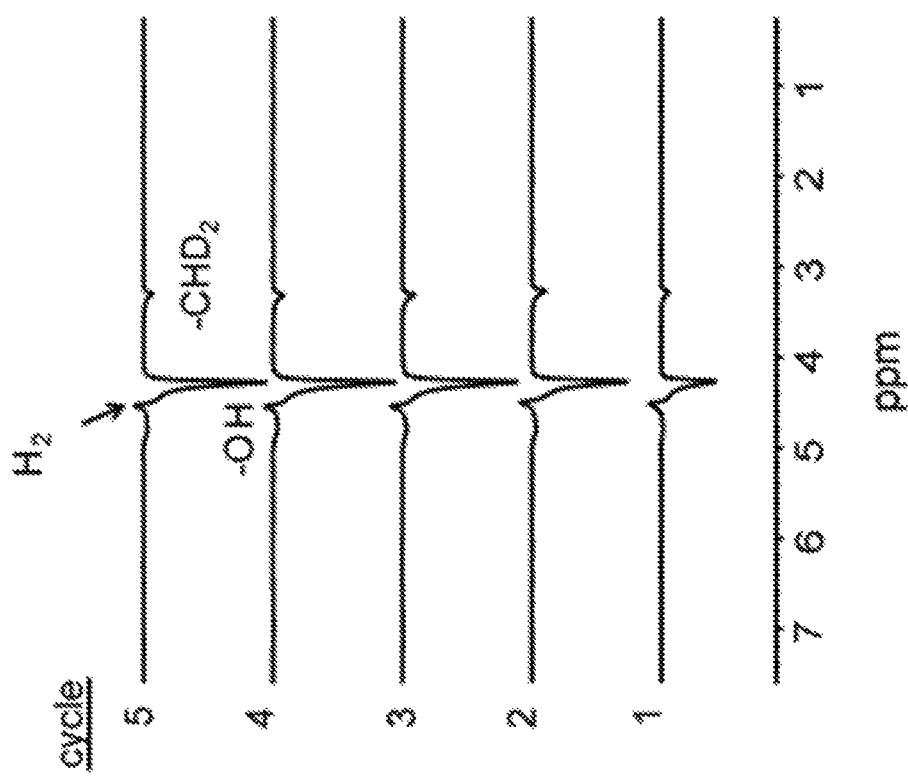

Clearly, H/D isotope exchange between $H_2$ and —OD deuterons is catalyzed on the surface of the $Pt_3Sn@mSiO_2$ catalyst, but is it the productive hyperpolarization mechanism? Polarization transfer could also be mediated by intermolecular spin-spin couplings, independent of H/D exchange. To differentiate between these two possible mechanisms, SWAMP spectra in methanol-$d_4$ were recorded as a function of the number of p-$H_2$ bubbling cycles, as shown in FIG. 3C, D. The —OH SWAMP emission peak increased monotonically up through 4 cycles. The decrease after the 5th cycle is attributed to destructive interference with the thermally polarized background absorption signal resulting from the accumulation of $CD_3OH$. In contrast, the —$CHD_2$ SWAMP signal did not significantly change over the course of 5 cycles. The SWAMP signals also increased with the number of cycles in the experiments in $D_2O$ (FIG. 13A). The dependence of the SWAMP signals of the exchangeable and non-exchangeable protons on proton isotopic fraction can be used to differentiate between the chemical exchange and spin exchange mechanisms, as shown below.

The NMR signal enhancement factors were estimated from the ratio of the SWAMP NMR peak to the peak integrals of the fully-relaxed $^1H$ spectra recorded before $H_2$ bubbling. Enhancement factors, before correction for relaxation losses, were −0.4 and −1.8 for the —OH protons in DOH and $CD_3OH$, respectively. We estimate $3 \times 10^{19}$ threefold Pt sites per gram of the $Pt_3Sn@mSiO_2$ catalyst. Hence, the water-to-surface site ratio in our samples is around 2000:1. Since the rate of exchange of water molecules between the surface adsorbed and bulk phase is unknown, there is a large uncertainty in the fraction of water molecules that are present only as spectators, contributing only to the thermally polarized signal. Higher enhancement factors can be expected with smaller particles with higher surface-to-volume ratio. Note that all the reported enhancement factors would have also been 3× larger had 99% para-enrichment been employed.

Discussion

Figures 7A, 7B:
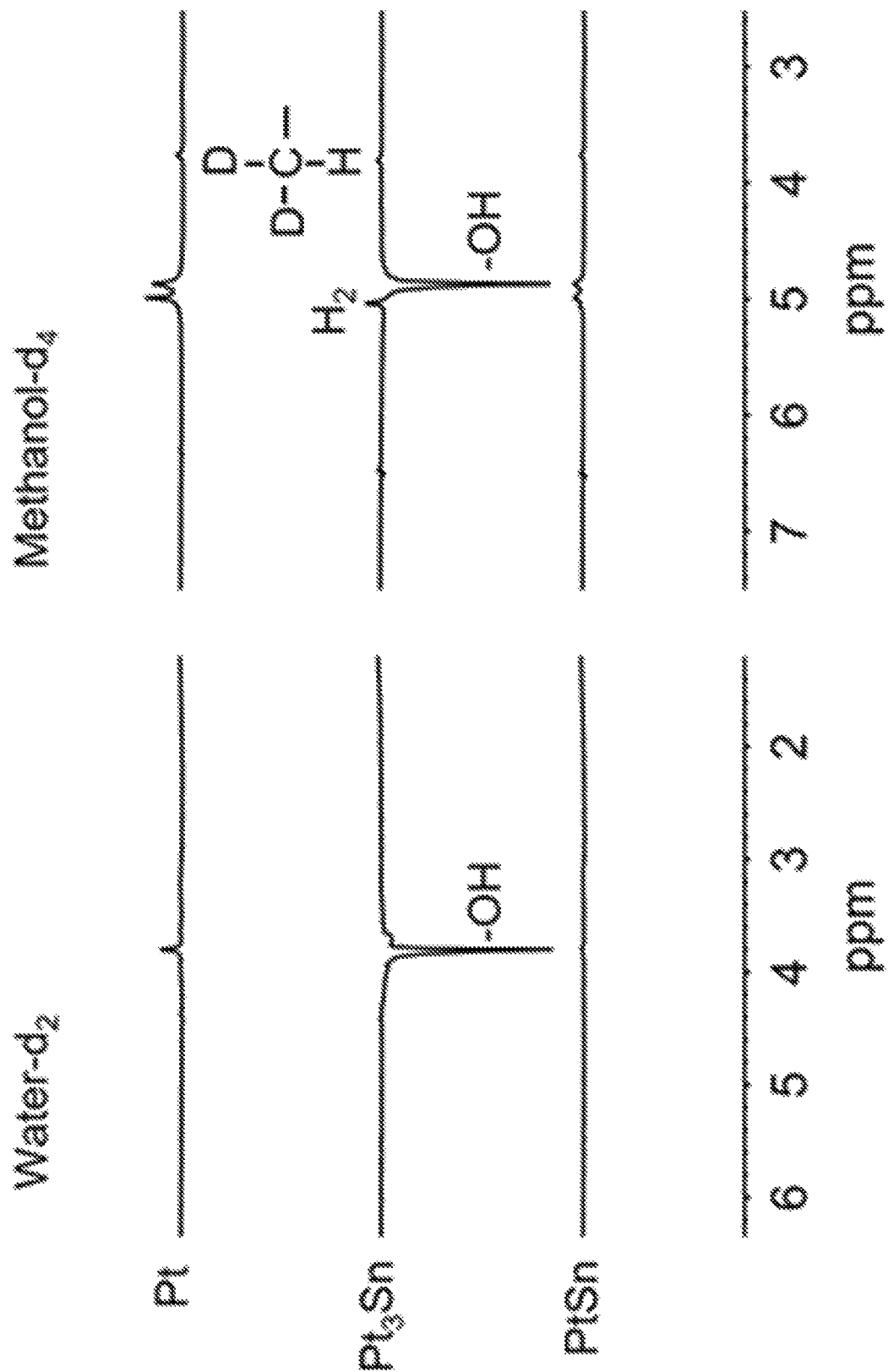
FIGS. 7A-7B are examples of single-shot 400 MHz $^1H$ NMR spectra of (A) water and (B) methanol acquired with a π/2 RF pulse immediately (within 10 s) after bubbling of 7 bar p-$H_2$ at 350 mL/min for 20 s through the liquids containing 50 mg of Pt@$mSiO_2$ (top), $Pt_3Sn$@$mSiO_2$ (middle) and PtSn@$mSiO_2$ (bottom) NPs. The temperature during bubbling in water and methanol is 120° C. and 105° C., respectively.
Figure 8:
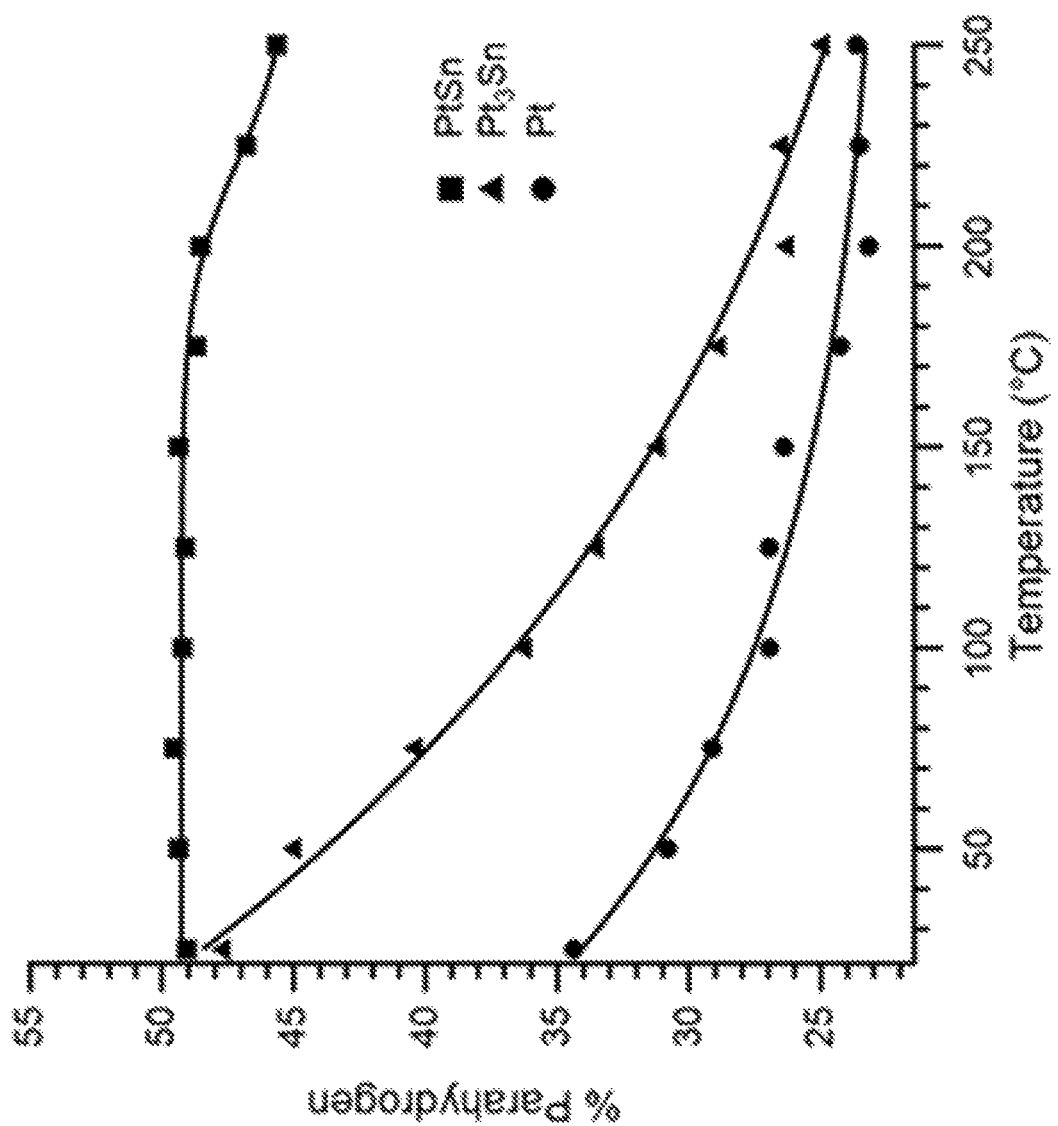
FIG. 8 illustrates temperature dependence of the percent parahydrogen content of $H_2$ gas, measured from the proton NMR, after passing 50% p-$H_2$ at 700 ml/min flow rate through a temperature controlled u-tube packed with 15 mg of Pt@$mSiO_2$, $Pt_3Sn$@$mSiO_2$, or PtSn@$mSiO_2$ nanoparticles.

Insight into the surface interactions that mediate the SWAMP effect can be gleaned from the high-vacuum surface science literature on well-defined Pt(111), p (2×2) $Pt_3Sn(111)$ and ($\sqrt{3} \times \sqrt{3}$)R30° $Pt_2Sn(111)$ surface alloys formed under high-vacuum conditions. Water, methanol and ethanol all adsorb weakly and reversibly on all three surfaces.[30-32] As noted above, facile dissociation of $H_2$ occurs on the three-fold hollow Pt(111) sites (FIG. 1C, D). Diffusion of H ad-atoms on the Pt (111) surface is very rapid (at our experimental temperatures) with a barrier of only ~5 kJ/mol, while diffusion on p(2×2) $Pt_3Sn(111)$ is hindered by a barrier of 41 kJ/mol due to the unfavorable interaction with Sn.[23] The novel synthesis of Pt, $Pt_3Sn$ and PtSn iNPs that mimic the model Pt—Sn surfaces allowed us to investigate the SWAMP effect on three-fold Pt sites that are contiguous, isolated, or absent. While $Pt_3Sn$ produced intense NMR emission peaks in water, methanol and ethanol, the Pt and PtSn catalysts produced no observable SWAMP signals (see FIGS. 7A-7B). Apparently, the surface structure of the $Pt_3Sn@mSiO_2$ iNPs optimizes the balance between facile $H_2$ dissociation and restriction of H ad-atom surface diffusion.[24,25,33] By restricting diffusion, the spin-spin coupling in the H ad-atom pair is prolonged. The results of a para→ortho back-conversion study (see FIG. 8) are consistent with this; $Pt@mSiO_2$ particles are most efficient in randomizing the p-$H_2$ singlet, while $PtSn@mSiO_2$ iNPs are ineffective at temperatures up to 175° C. The trend in the back-conversion is opposite to that of the pairwise selectivity of propene hydrogenation: Pt<$Pt_3Sn$ <PtSn.[22]

H/D exchange between co-adsorbed $H_2$ and $D_2O$ (or $D_2$ and $H_2O$) has not been previously studied on Pt—Sn, but it was investigated on Au(111) surfaces.[34] Temperature programmed desorption (TPD), reflection-absorption infrared spectroscopy (RAIRS), and density functional theory (DFT) calculations suggest that isotope exchange is mediated by protonated water clusters, $(H_2O)_nH^+$, with reversible electron transfer to the metal:

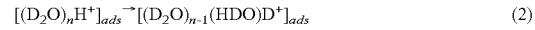

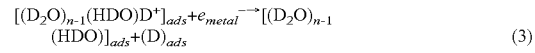

The hydronium-like species have also been identified on Pt surfaces.[35,36] It is likely that the observed H/D exchange between co-adsorbed $H_2$ and the —OD groups in hydrogen-bonded networks of $CD_3OD$ or $CD_3CD_2OD$ on the $Pt_3Sn@mSiO_2$ occurs by this mechanism.

Figures 5A, 5B, 5C:
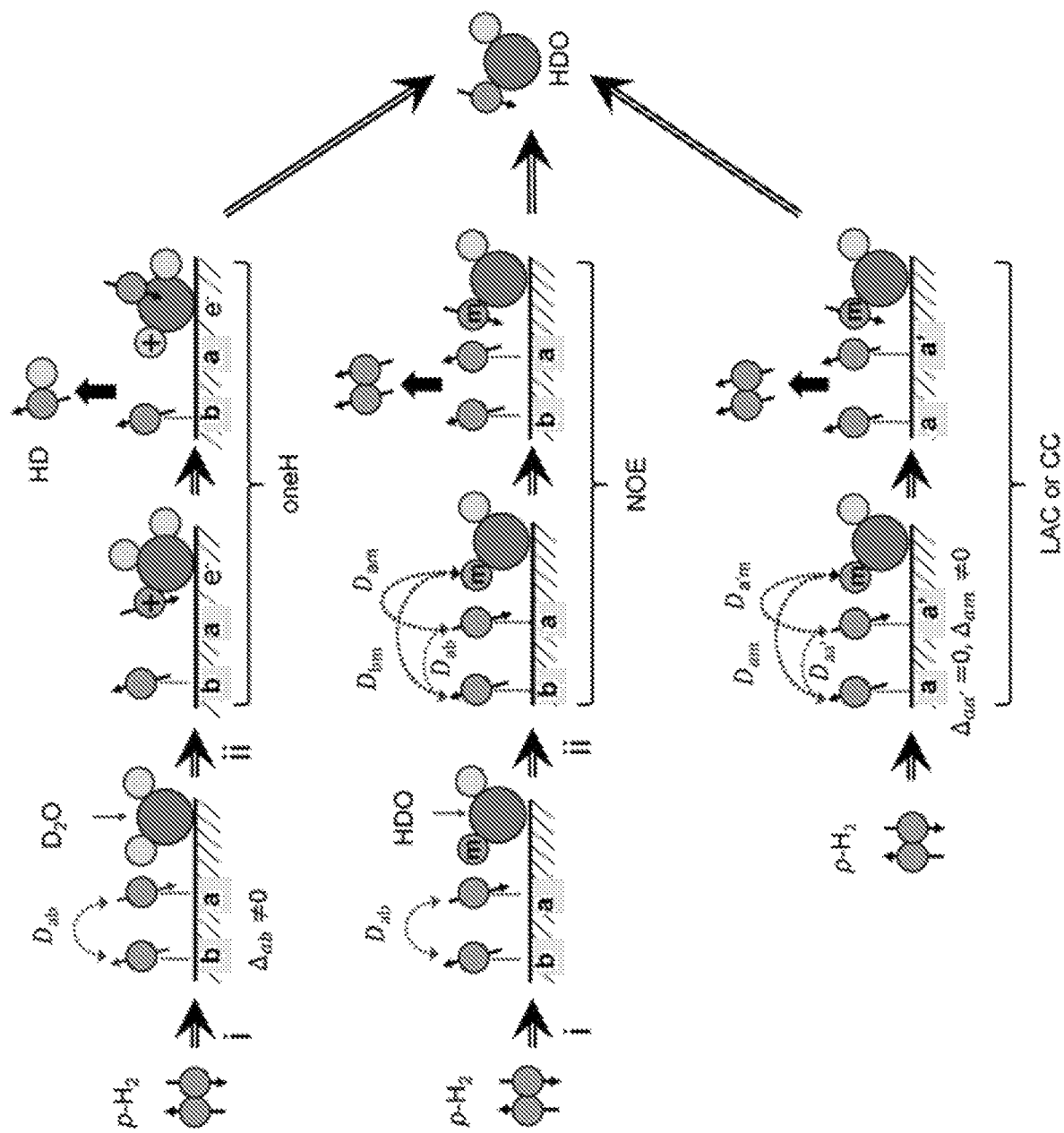
FIGS. 5A-5C show examples of three mechanistic models for hyperpolarization of HDO from p-$H_2$. (A) oneH, where spin polarization transfer occurs via single H/D exchange between co-adsorbed p-$H_2$ and $D_2O$. (B) Spin polarized nuclear Overhauser Effect (SWAMP-OE) via unequal dipolar couplings. In both mechanisms, the magnetic equivalence of p-$H_2$ is broken by dissociation and chemisorption into strongly coupled, magnetically inequivalent adsorption sites (a and b) with dipolar coupling $D_{ab}$ and chemical shift difference $\Delta_{ab}$. $D_{am}$ an $D_{bm}$ are the dipolar couplings to the —OH proton. (C) Coherence transfer via level anti-crossing (LAC) due to the inequivalent dipolar couplings between the strongly coupled H ad-atom pair in chemically equivalent sites (a and a') and the HDO proton (m). Here, the m protons on the HDO molecules are assumed to be initially unpolarized, as indicated by the absence of a spin vector on the H atom. Spin-exchange by LAC is productive only for the m protons initially in the spin-up state, such that total spin angular momentum is conserved. Cross-correlation (CC) is an incoherent process that does not require chemically inequivalent adsorption sites for the H ad-atom pair.

FIGS. 5A-C presents four hypothetical mechanisms that could explain the hyperpolarization of HDO from p-$H_2$ on the $Pt_3Sn$ surface. Path A is a "oneH" type mechanism[12] that occurs in two sequential steps: (i) dissociative chemisorption of p-$H_2$ into strongly coupled, chemically inequivalent sites (labelled a and b) followed by (ii) single H/D exchange with $D_2O$. In the literature, a oneH mechanism was invoked to explain the $^1H$ net emission signals in the solution-state hydroformylation catalysis on Pt and Ir carbonyl complexes at high magnetic field,[37] where the single H transfer to the substrate occurs via a strongly coupled dihydride intermediate. On the $Pt_3Sn$ surface, the time-evolution of the strongly-coupled H ad-atom proton pair, when averaged over the kinetic distribution of adsorption events, results in a complete loss of spin coherence and unequal probability densities for the $|\alpha\rangle$ and $|\beta\rangle$ spin states at each site. In the second step, one H ad-atom of the pair is exchanged with a D atom preferentially from one type of adsorption site. The sign of the polarization depends on the sign of the chemical shift difference relative to the dipolar coupling. Path B presents a sequential NOE mechanism. As in path A, proton spin coherence in the H ad-atom pair is destroyed by kinetic averaging over adsorption times. The subsequent polarization transfer to the HDO proton is mediated by the Nuclear Overhauser Effect (NOE) with differential rates of cross-relaxation between the H ad-atom protons to the HDO proton. Path C illustrates the interactions involved in a Level Anti-Crossing (LAC) mechanism[38] where coherence transfer is induced by mixing of the spin states of the H ad-atom pair and the HDO proton. Unequal dipolar couplings to the HDO proton would result from different internuclear distances. The mixing of the HDO and $H_2$ spin states is maximized at the LAC, where the dipolar coupling in the adsorbed H pair matches the chemical shift difference of the HDO proton and the adsorbed H atoms (i.e. $D_{aa} \approx \Delta_{am}$). The spontaneous and incoherent conversion of singlet spin order into magnetization in the case of a chemically equivalent H ad-atom pair can also occur through a cross-correlation (CC) nuclear relaxation interference mechanism, as proposed by Aime et al. to explain net polarization of hydrides constituting an $A_2$-system in PHIP experiments.[39]

The essential spin dynamics for paths A and B in FIGS. 5A-5B can be qualitatively modelled by a system of two spins-1/2 system with dipole-dipole coupling $D_{ab}$. For simplicity, the dipolar couplings to $^{195}Pt$, $^2H$, and other nearby protons will be neglected. Complete details of the density matrix calculation, which is briefly outlined here, are provided in the supporting information (SI). The general eigenbasis of this spin system is $\{|\alpha\alpha\rangle, |2\rangle \equiv c_1|\alpha\beta\rangle + c_2|\beta\alpha\rangle, |3\rangle \equiv -c_2|\alpha\beta\rangle + c_1|\beta\alpha\rangle, |\beta\beta\rangle\}$, where $c_1 = \cos \kappa/2$, $c_2 = \sin \kappa/2$, and $\tan \kappa = D_{ab}/\Delta_{ab}$, where $\Delta_{ab}$ is the difference in the chemical shifts imparted by the distinct surface adsorption sites. The parameter K characterizes the "strength" of the spin-spin coupling. In the singlet, $\kappa \rightarrow \pi/2$. Upon dissociative chemisorption into adsorption sites that render the protons chemically inequivalent, K changes suddenly. The eigenstate populations can be calculated assuming the sudden approximation. The density matrix $\rho^{ads}$ for the adsorbed proton pair is obtained by expressing the density operator for $H_2$ with an arbitrary para-enrichment, $\hat{\Sigma}^{H_2} = x_p \hat{\rho}^{para} + (1-x_p) \hat{\rho}^{ortho}$, in the arbitrary-$\kappa$ eigenbasis. The coherences $\rho_{23}^{ads}$ and $\rho_{32}^{ads}$ (i.e. off-diagonal elements of $\rho^{ads}$) are set to zero to model the time-averaging over the kinetic distribution of chemisorption events, yielding the time-averaged density matrix $\bar{\rho}^{ads}$ in Eq. (S13). On the oneH mechanism, H/D exchange can generate hyperpolarized HDO only if the magnetically inequivalent H adsorption sites have unequal propensities for oxidation/hydration. Assuming exchange with the a-site proton:

$$P_{HDO} = 2\langle I_{za} \rangle = 2Tr(I_{za}\bar{\rho}^{ads}) = \frac{1}{6}(1-4x_p)\sin(2\kappa) \quad (4)$$

If the remaining proton at the b-site recombines with the exchanged deuteron to form HD without significant relaxation, hyperpolarized HD would be produced with opposite signal phase:

$$P_{HD} = -P_{HDO} \quad (5)$$

For $x_p = \frac{1}{2}$, $$P_{HDO} = -\frac{1}{6}\sin(2\kappa),$$

corresponding to a negative spin temperature and stimulated emission signals. As noted above, a 3-fold larger polarization would be obtained using pure p-$H_2$. On the metal nanoparticle surface, where molecular motion is anisotropic and spin interactions retain the tensorial forms, $\kappa$ would generally depend on the orientation of the catalyst surface with respect to the applied field, and the density matrix $\bar{\rho}^{ads}$ would also need to be spatially averaged over all orientations relative to the magnetic field.[40]

Equation 4 is also relevant to the interpretation of the polarization transfer by the sequential NOE mechanism (path B, FIG. 5B), where the kinetic averaging of the density matrix of the strongly-coupled H ad-atom pair is assumed to occur on a time-scale that is short compared to the NOE buildup time. A non-zero $P_{HDO}$ is obtained only if the two cross-relaxation rates to the m proton differ, as would be the case for unequal distances and dipolar couplings to the a and b adsorption sites. The qualitative model further predicts that $P_{HDO}$ is maximized when $\kappa \rightarrow \pi/4$ (i.e. $D_{ab} \approx \Delta_{ab}$). In addition to the powder averaging of the polarization in Eq. 4 over the distribution of surface orientations, the NOE cross-relaxation rate can also be expected to be anisotropic. At high field, where the H ad-atom pair would likely exist as a weakly coupled AX spin system ($\kappa \rightarrow 0$), the singlet state projects equally onto the $|\alpha\beta\rangle$ and $|\beta\alpha\rangle$ states, yielding zero SWAMP signal. Near zero field, where $\kappa \rightarrow \pi/2$, Eq. (4) predicts $P_{HDO} = 0$.

Figure 9:
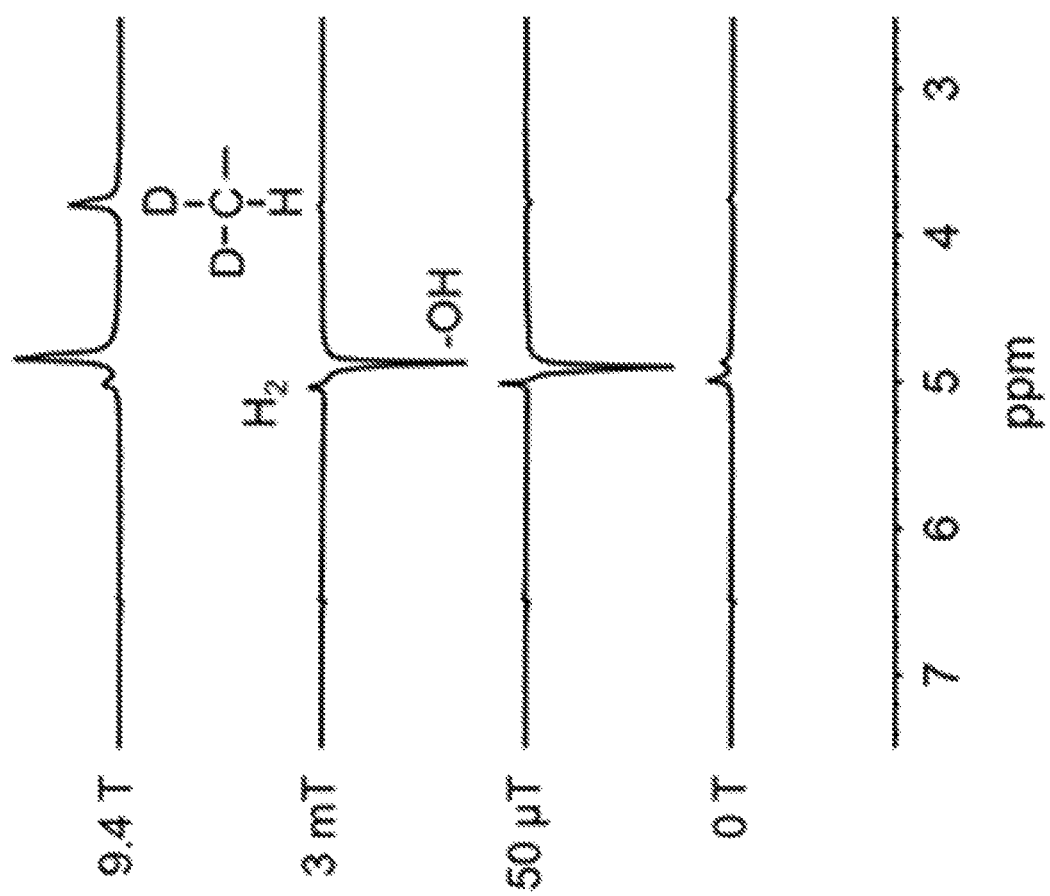
FIG. 9 is an example 400 MHz $^1H$ NMR spectra obtained using 50 mg $Pt_3Sn$@$mSiO_2$ in methanol-$d_4$ after bubbling p-$H_2$ at 350 mL/min for 20 s at near-zero, earth magnetic field (~50 µT), 3 mT and 9.4 T. A 90 o pulse was applied to acquire each spectrum.

A preliminary field dependence of the SWAMP effect in methanol-$d_4$ was obtained by performing experiments at a series of four conveniently accessible magnetic fields: near-zero field, earth's field ($\approx 50$ μT), the fringe of the NMR magnet (3 mT) and high field (9.4 T). Enhanced net emission NMR signals were observed only at 50 μT and 3 mT but bubbling at near-zero field or 9.4 T produced no discernable SWAMP signals (FIG. 9). The lack of a SWAMP effect near zero field suggests that symmetry-breaking Zeeman interactions are required, while its absence at high field indicates the importance of strong spin-spin coupling. Despite the multiple simplifying assumptions, Eq. (4) is qualitatively consistent with the absence of any SWAMP signal at near zero field or high field. The LAC mechanism (FIG. 5C) is also expected to be ineffective at zero field or high field. However, the field dependence of the LAC polarization transfer also depends on the dipolar contact time, chemical shift difference, and spin couplings,[41] as well as the relative-orientation of the surface adsorbates and their orientation with respect to the magnetic field. Without a complete knowledge of these spin interactions, the molecular geometry, and relative distances between the relevant nuclei in the co-adsorbates, and molecular dynamics on the surface, we did not attempt to calculate the detailed LAC field dependence. As demonstrated in Ref 42, the efficiency of the CC mechanism involving chemically equivalent H ad-atom pair increases with magnetic field, which is inconsistent with the observed magnetic field dependence of the SWAMP effect.

The foregoing analysis suggests that the magnetic field dependence of the SWAMP signal cannot be used to differentiate between the hypothesized mechanisms. However, other experimental evidence, together with statistical considerations, does afford a further elucidation of the mechanism. In a chemical exchange-mediated polarization transfer mechanism, the deuteron or unpolarized proton of the hydroxy group of the water or alcohol molecule is replaced, irrespective of the isotope that is initially present, with a hyperpolarized proton. In contrast, hyperpolarization of the non-exchangeable protons requires spin-spin interactions. Intramolecular spin coupling (dipolar or scalar) mediated polarization transfer from —OH to non-exchangeable protons is ruled out based on the (i) vanishingly small probability for simultaneous protonation of both sites on the same molecule (c.a. $\frac{1}{10^6}$, for a 99.8% total D enrichment) and (ii) rapid exchange of the —OH proton. Therefore, hyperpolarization of the non-exchangeable protons is mediated by the intermolecular dipole-dipole couplings to the H ad-atoms. As noted above, the intensities of the SWAMP NMR signals at the exchangeable and non-exchangeable positions (in the alcohols) are of the same order of magnitude, even though only 0.1% of the molecules contain a non-exchangeable impurity proton. This is statistically inconsistent with polarization transfer via H/D exchange, and consistent with an intermolecular dipole-dipole mediated mechanism for both the exchangeable and non-exchangeable protons. This conclusion is further supported by the observed dependence of the —OH SWAMP signal on the proton fraction, which increases with the number of bubbling cycles. In an exchange-mediated mechanism, —OH SWAMP signal would be independent of the initial —OH fraction. In contrast, the NOE and LAC mechanisms require a pre-existing proton on the polarization target molecule and are thus expected to scale in proportion to proton fraction. FIGS. 3 and 13A-13C clearly show that the SWAMP signal increases monotonically with the proton isotope fraction. The observed SWAMP emission signal increases with the number of bubbling cycles despite the increasing destructive interference from the absorption signal of the thermally polarized spectator water molecules. In a chemical exchange-mediated polarization transfer process, the total emission signal would only decrease with increasing proton isotope fraction because the SWAMP signal contribution remains constant while the thermal signal grows with the number of bubbling cycles. Hence, we conclude that the SWAMP effect on the $Pt_3Sn@mSiO_2$ catalyst is mediated by the intermolecular dipolar couplings to surface-adsorbed H. The lack of any signal enhancement for the methyl proton in ethanol is explained by its greater distance away from the surface, since the alcohol is most likely bound to the surface of the nanoparticle through the Sn—O interaction.[9] The lack of a hyperpolarized dissolved HD peak is also consistent with an H/D exchange process that is unproductive as a hyperpolarization mechanism. In principle, hyperpolarized o-$H_2$ is produced in the LAC and NOE effects, but was not observed in our experiments. This could be due to a combination of factors: the short spin relaxation time (ca. 2 s in methanol-$d_4$[19]) relative to the 10s transport time in our experiments; rapid $T_1$ relaxation of ortho-$H_2$ on the surface; scrambling of the spin-state by recombination with other H ad-atoms by the same process that accounts for the high ortho-para conversion efficiency on the $Pt_3Sn@mSiO_2$ iNPs.

While somewhat beyond the scope of the present work, it is nevertheless interesting to explore the possible relationship between the SWAMP polarization transfer mechanism for our $Pt_3Sn@mSiO_2$ catalyst and the reported hyperpolarization of water[21] and methanol[43,44] using the homogeneous iridium catalysts under SABRE conditions. Lehmkuhl et al.[21] reported that in the presence of L-histidine in $D_2O$, both hyperpolarized HDO and HD are observed. The HDO exhibited a maximum emission peak at a polarizing magnetic field of around 40 mT, while no hyperpolarization was observed at high field. This does not necessarily rule out the oneH mechanism since the hydride protons of their histidine-bound Ir complex are weakly coupled in high field. Moreover, the observation of hyperpolarized HD peaks that are opposite in phase with respect to the HDO emission peak is also consistent with a oneH mechanism (see Eq. (5)) but can also be explained in terms of a NOE or LAC effect. Earlier SABRE studies reported enhancement of the —OH and methyl impurity protons of the 99.97% enriched $CD_3OD$ solvent under acidic conditions using homogeneous Ir-based catalysts.[43,44] The hyperpolarization of the —OH proton was attributed to proton exchange with hyperpolarized free pyridine, but additional observations, including the solvent enhancement in pyridine-$d_5$ and a prolonged relaxation time after transferring the sample to high field, led the authors to conclude that an additional mechanism is also active, i.e. NOE cross-relaxation between the hyperpolarized hydride protons and the protons of methanol directly coordinated in the Ir complex. A CC/NOE type mechanism has been proposed to explain the SABRE polarization enhancement of pyridine and ortho-$H_2$ at 9.4 T.[19,42] The possibility of a oneH mechanism involving H/D exchange was not considered but is deemed unlikely in view of the magnetic equivalence of the hydride protons in their catalyst when the pyridine-$^{14}N$ substrate is used.

Before closing, we briefly review some of the interesting applications of the SWAMP effect. Hyperpolarized liquid water, which can be produced by Dynamic Nuclear Polarization (DNP) techniques,[45-47] has been touted as an "authentic" contrast agent to study localized angiography and brain perfusion.[48,49] Its use in biomolecular NMR is an emerging hot-topic.[50] In the Water-LOGSY NMR experiment, used in drug-discovery to detect protein-ligand interactions, the protein NMR signals are greatly enhanced by injecting hyperpolarized water into solutions of proteins and ligands.[47] SWAMP could also be used for such spectroscopic applications, with greater simplicity, scalability, portability, and reduced cost. Hyperpolarization of methanol and ethanol was also demonstrated, indicating that the SWAMP technique can be extended to other molecules. A list of substances that were tested but did not exhibit SWAMP signals under the experimental conditions described herein is provided in Table 2.

Figures 6A, 6B:
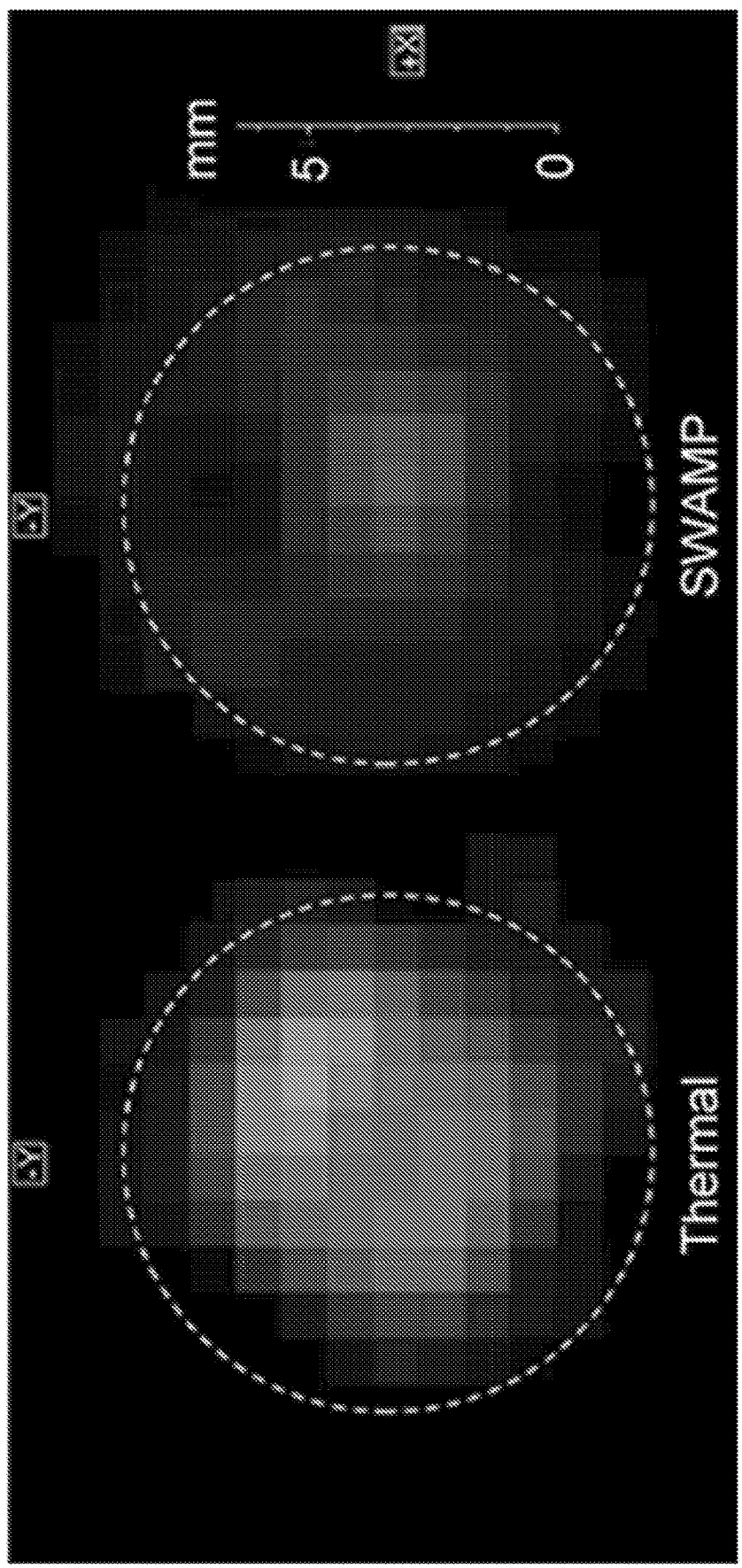
FIGS. 6A-6B are example $^1H$ images of a medium-wall 10 mm O.D. NMR tube containing a mixture of 900 D2O, 900 CD3OD, and 100 mg $Pt_3Sn$@$mSiO_2$ iNPs, recorded at 750 MHz using the SPIRAL-EPI pulse sequence A. Thermally polarized; B. world's first SWAMP-hyperpolarized image. Orange=absorption, Blue=emission (negative phase).
Figure 15:
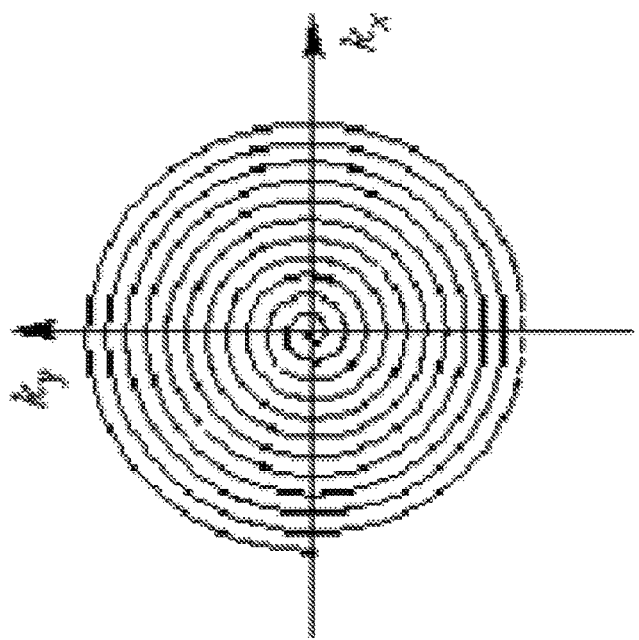
FIG. 15 provides an example of a spiral-EPI acquisition of the present disclosure. A single excitation pulse is used with a spiral center-out k-space trajectory. This sequence will allow for accurate measurements of 1'1-maps of the samples and monitoring the decay of hyperpolarized signal.
Figure 15:
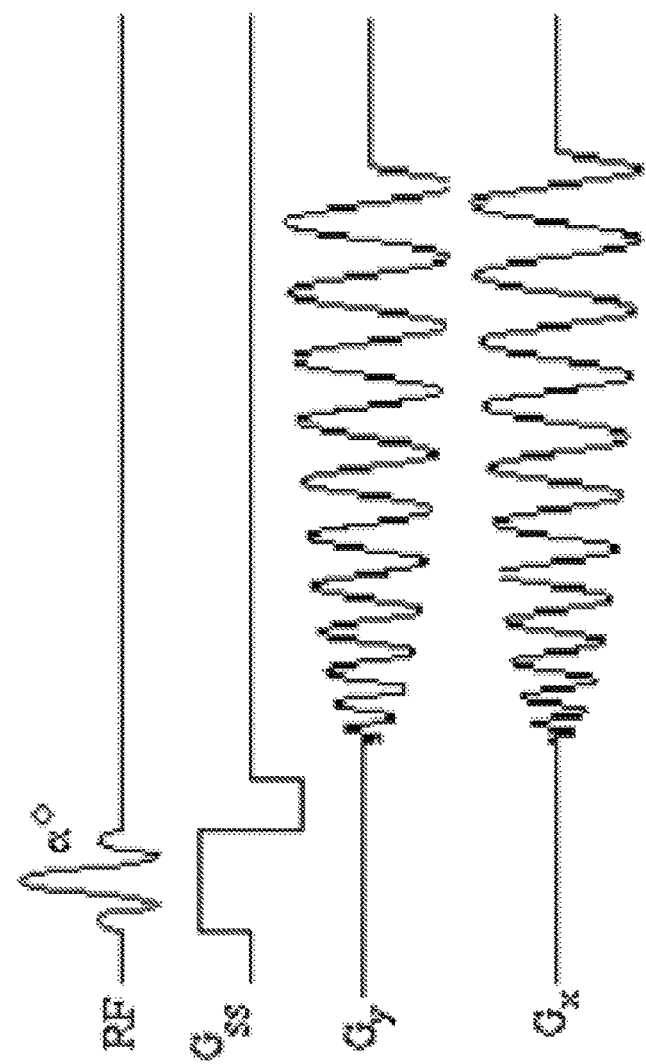

As a proof-of-principle demonstration of MR imaging, the world's first SWAMP $^1H$ image, recorded at 750 MHz, is presented in FIG. 6B. For comparison, the thermally polarized image of the same sample acquired under identical conditions except with argon gas bubbling is shown in FIG. 6A. The MR images were acquired with a standard SPIRAL-EPI[51] acquisition (FIG. 15), with a single 90° excitation pulse. The phase used to color the images was calculated from the first recorded data point in the spiral acquisition, where no gradients are applied, and the signal is proportional to the total signal present in the sample. At this extremely high magnetic field, the thermally polarized image at 17.6 T is better than the one recorded using SWAMP pre-polarized water. However, SWAMP images are expected to be far superior at lower fields, since the Boltzmann polarization (in the Curie-Law regime) scales proportionally with field.[52] Moreover, higher SWAMP hyperpolarization is likely to be achieved by improved catalyst synthesis (e.g. smaller catalyst particle size), higher p-$H_2$ enrichment, and optimization of reaction conditions. Low-field MRI could be the most promising application for SWAMP.

A key advantage of our heterogeneous $Pt_3Sn@mSiO_2$ catalyst is its insolubility, which allows it to be quickly and completely separated from the hyperpolarized water without any leaching, as previously shown.[22] This remains a non-trivial problem for dissolved catalyst complexes.[21,53] SWAMP can generate NMR-observable hyperpolarization of liquids that are free of free radicals, catalyst residues or other additives at low magnetic field. This could enable low field MRI without superconducting magnets[52] which could enable wider access of this powerful medical diagnostic technique in remote or impoverished regions.

Experimental Procedures

Synthesis of Monometallic $Pt@mSiO_2$ NPs.

The $mSiO_2$-encapsulated Pt NPs ($Pt@mSiO_2$) were prepared according to the previously reported literature[22]. Briefly, around 25 mL of a 10 mM $K_2PtCl_4$ was added to 200 mL of a 125 mM aqueous solution of tetradecyltrimethylammonium bromide. The above mixture was stirred for 10 minutes and then moved to an oil bath maintained at 50° C. for 10 minutes. 25 mL of 300 mM sodium borohydride solution prepared in ice-cold water (Alfa Aesar, 98%) was then added. After the solution was stirred for 20 h at 50° C., the dark brown solution was centrifuged at 3000 rpm four times for 30 min, with the supernatant being collected while the residue was discarded. Finally, the supernatant was centrifuged at 14000 rpm for 15 min twice, collected, and redispersed in deionized water to obtain around 200 mL of the solution. About 1 mL of a 1 M sodium hydroxide solution was added to obtain a pH between 11 and 12. While stirring, 3 mL of a 10% tetraethyl orthosilicate solution in methanol was added dropwise via syringe. After 24 h, the sample was centrifuged at 14000 rpm twice, and the coated particles ($Pt@mSiO_2$) were redispersed in 200 mL of methanol. 10 mL of hydrochloric acid (36% assay) was added and the solution was refluxed at 90° C. for 24 h.

Synthesis of Intermetallic $Pt_3Sn@mSiO_2$ and $PtSn@mSiO_2$ NPs.

The methanol-dispersed solution of $Pt@mSiO_2$ was centrifuged and redispersed in 75 mL of tetraethylene glycol (Alfa Aesar, 99%) in a 250 mL two-neck flask. The amount of Pt in a typical synthesis of Pt@mSiO$_2$ particles was 0.15 mmol. To ensure a Pt:Sn molar ratio of 3:1, SnCl$_2$.2H$_2$O (Alfa Aesar, 98%) was used as the source of Sn, and the solution was heated at 280° C. for 2 h to form the alloy. Subsequently, an equal volume of acetone was added and sonicated to obtain a homogeneous solution. The solution was then centrifuged at 14000 rpm and calcined at 500° C. for 4 h to remove any remaining organic residues in the NPs. The calcined sample was then reduced at 600° C. for 4 h in a 10% H$_2$/Ar flow in a tube furnace to obtain intermetallic Pt$_3$Sn@mSiO$_2$. PtSn@mSiO$_2$ was prepared with a molar ratio of Pt:Sn=1:1 using the same precursor. After the same procedures until calcination at 500° C., the sample was then reduced in 10% H$_2$ in a tube furnace at 300° C. for 4 h to obtain intermetallic PtSn@mSiO$_2$. Inductively coupled plasma mass spectrometry (ICP-MS) measurements were also carried out on the powdered samples to confirm their stoichiometry as per the synthesis.

Transmission Electron Microscopy.

Bright field TEM images were recorded with a TECNAI G2 F20 microscope with an acceleration voltage of 200 kV. Atomic resolution HAADF-STEM images were acquired using an FEI Titan Themis 300 probe-corrected scanning transmission electron microscope (STEM) at an acceleration voltage of 300 kV. Before the TEM measurements, all the samples were first calcined at 500° C. and then reduced at the appropriate temperature in a 50 mL/min 10% H$_2$ in Argon stream.

SWAMP NMR Experiments.

Figure 10:
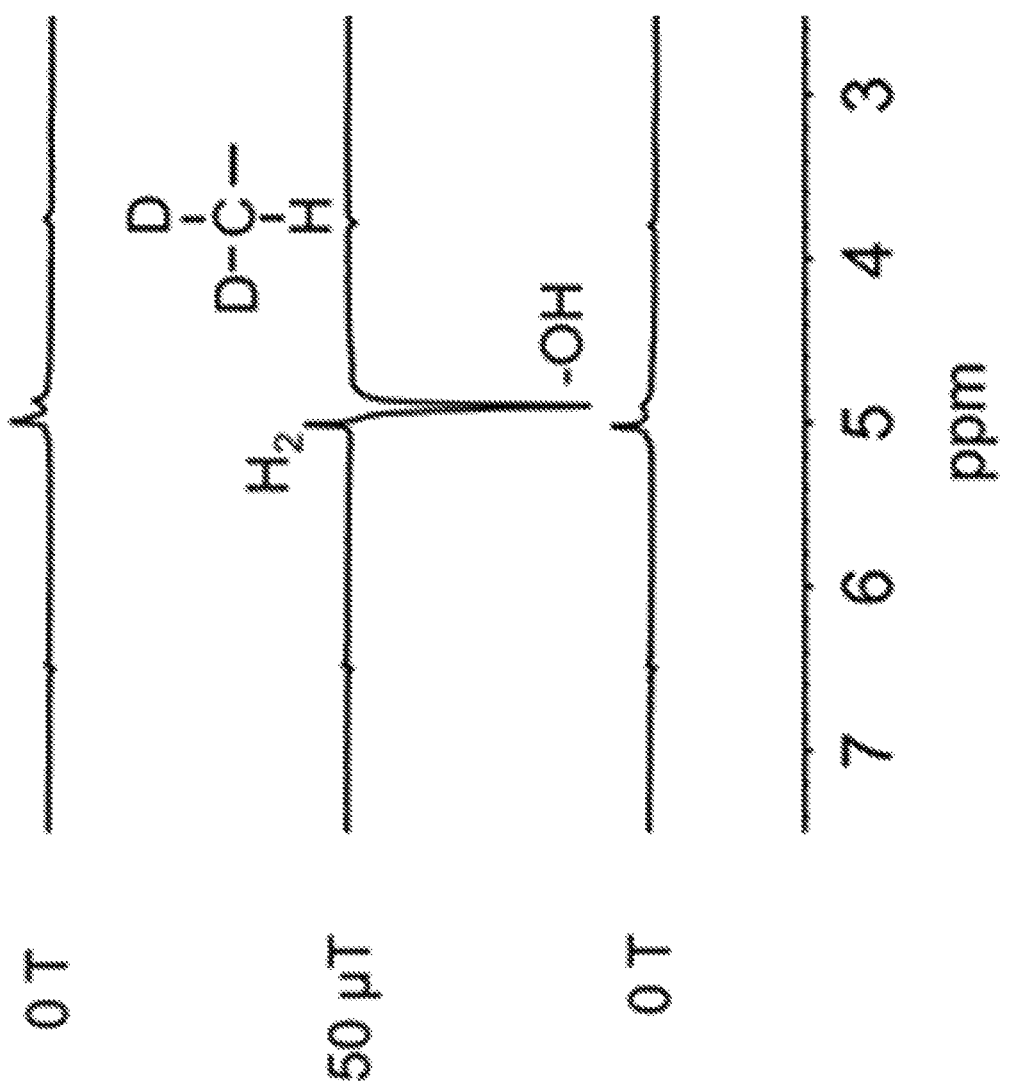
FIG. 10 is an example 400 MHz $^1H$ NMR spectra obtained using 50 mg $Pt_3Sn$@$mSiO_2$ in methanol-$d_4$ after bubbling p-$H_2$ at 350 mL/min for 20 s at 0 T, 50 µT and 0 T consecutively.

Using the NMR tube slurry reactor that was described in detail in our previous report[22], low field SWAMP NMR spectra in D$_2$O, CD$_3$OD and CD$_3$CD$_2$OD were acquired following bubbling p-H$_2$ gas at earth magnetic field (50 µT). The NMR tube was loaded with 50 mg of insoluble catalyst powder in deuterated water, methanol and ethanol. The solution was de-oxygenated by bubbling N$_2$ at a flow rate of 50 mL/min for 5 min. The head-space of the NMR tube was purged with p-H$_2$ gas for 2 min at a flow rate of 300 mL/min. The NMR tube was then pressurized to 7 bar with p-H$_2$ and immersed in a hot oil bath at set temperatures for 15 min prior to reactions. After bubbling p-H$_2$ gas through the slurry for 20 s at a flow rate of 350 mL/min, a back pressure was applied to stop the bubbling immediately. The NMR tube was then manually inserted into a 10 mm liquid probe in a 400 MHz magnet as quickly as possible (~10 s) and a single free induction decay was acquired using a 90° pulse. The thermally polarized spectra presented in FIG. 2 were acquired using the same procedure except that n-H$_2$ was bubbled through the fresh solution. The fully relaxed thermally polarized spectra of methanol and ethanol (FIG. 4) were collected 180 s after insertion of samples. The SWAMP experiments involving bubbling of p-H$_2$ at 9.4T were performed with the sample inserted in the Bruker 10 mm liquid probe inside the magnet. The probe was heated to 80° C. by a variable-temperature control system of the NMR spectrometer. Then the procedures that are the same to the low field experiments were performed followed by a 90° pulse. For the near-zero field experiments, the NMR tube was pre-heated to 80° C. in an oil bath for 15 min and the oil bath with the NMR tube in it was manually transferred to a three-layer concentric µ-metal shield as quickly as possible, followed by bubbling p-H$_2$. The temperature of the oil bath was measured to be 78° C. after bubbling gases. To ensure the reproductivity of the near-zero field experiment, two consecutive near-zero field experiments were performed immediately before and after an experiment at earth magnetic field (FIG. 10). For the experiment performed at 3 mT, the solution was positioned at the fringe field of the Bruker Avance Ultrashield 89 mm bore 9.4T superconducting NMR magnet and the field strength was measured using a LakeShorei'm Gaussmeter.

To unambiguously confirm the chemical origin of our hyperpolarized signal, pyridine-d$_5$ was added into the solution as an internal standard.[19] This technique was used to identify hyperpolarized orthohydrogen (o-H$_2$) in a solution of pyridine and N-heterocyclic carbene complex-based Ir catalyst in methanol-d$_4$.

Figure 11:
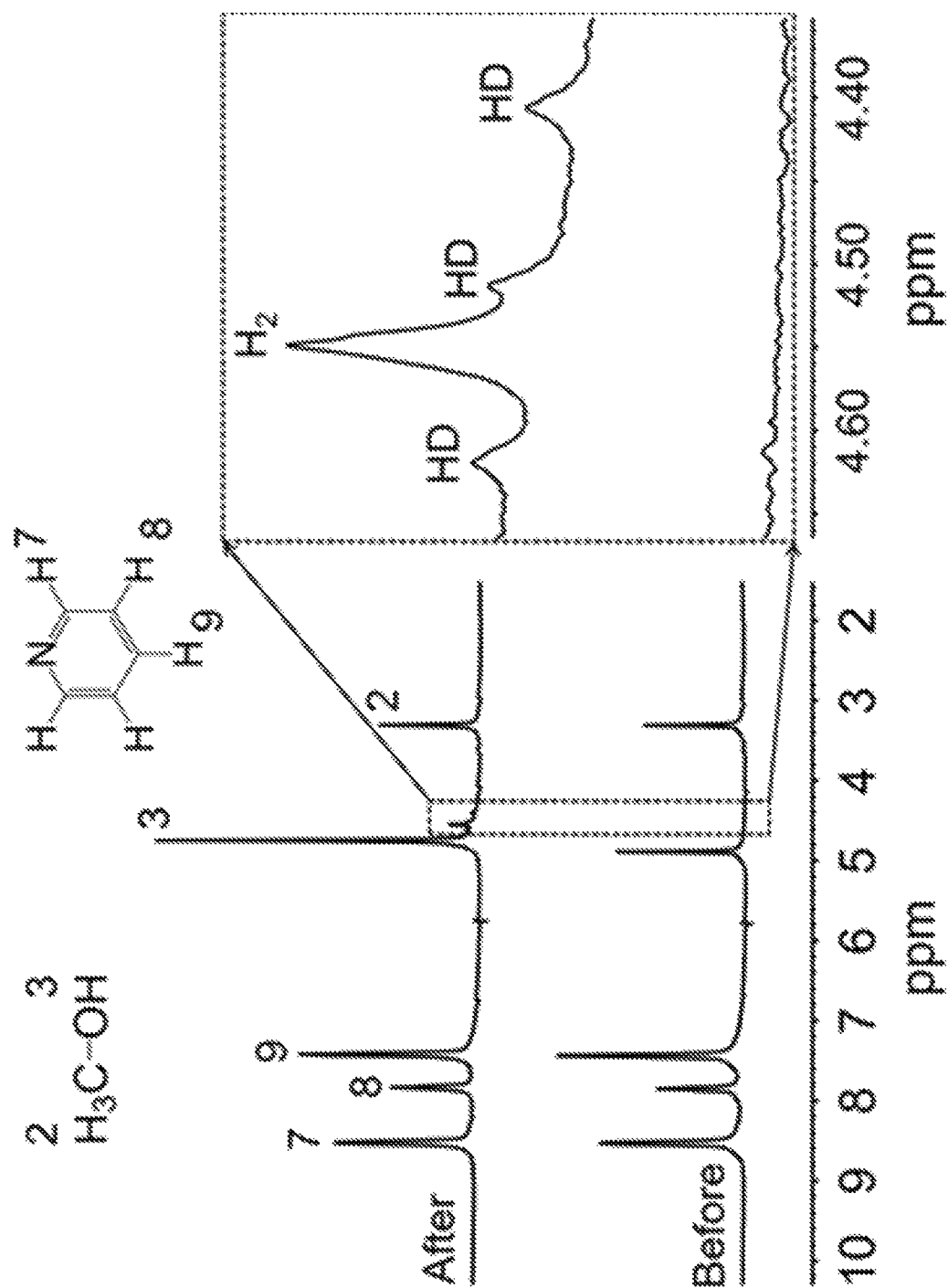
FIG. 11 is an example of a fully relaxed thermally polarized $^1H$ NMR spectra acquired before and after bubbling p-$H_2$ through a mixture of methanol-$d_4$ and pyridine-$d_5$ and $Pt_3Sn$@$mSiO_2$ at 105° C.
Figures 12A, 12B, 12C:
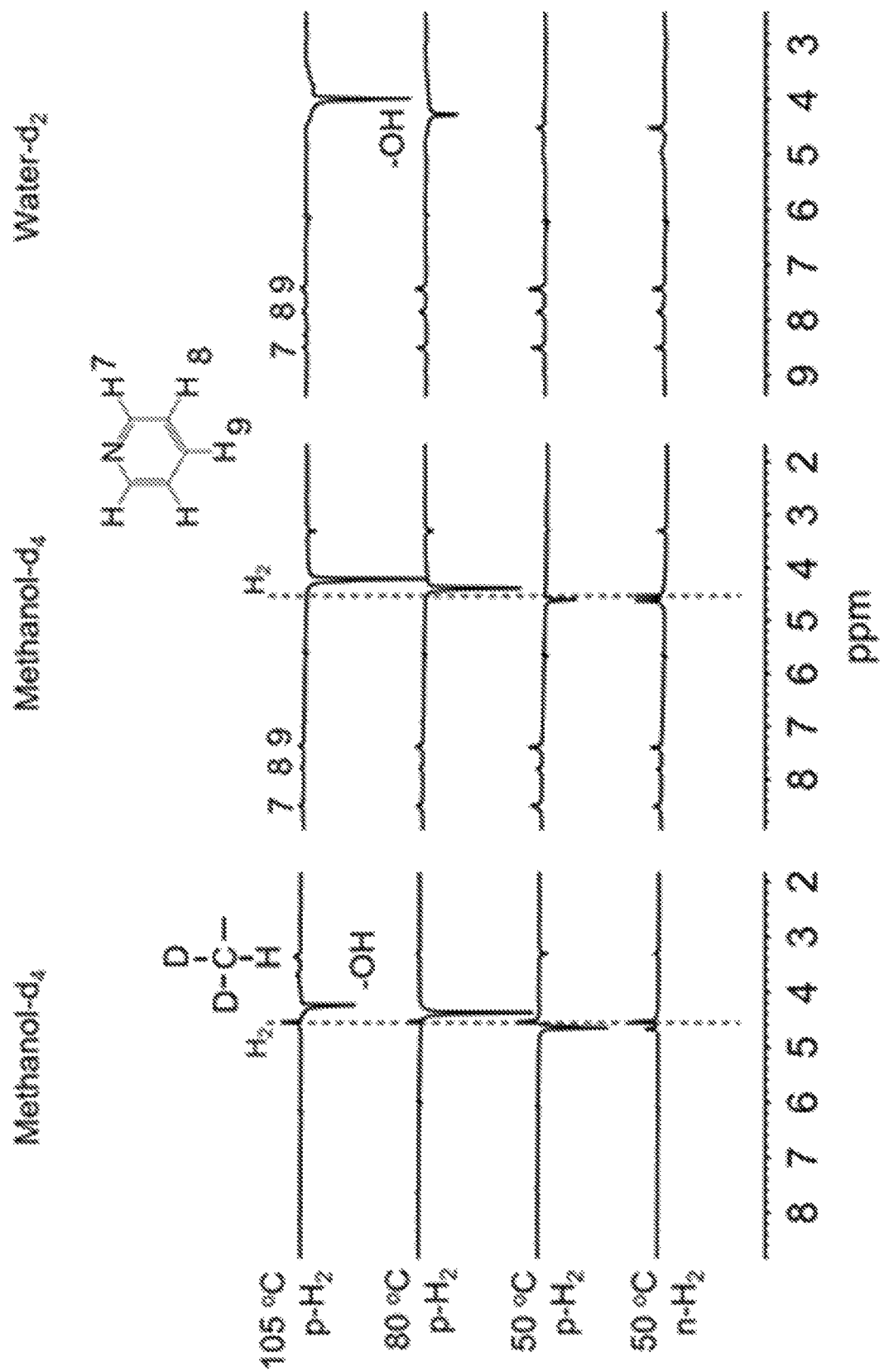
FIGS. 12A-12C are examples of $^1H$ NMR spectra obtained using 50 mg $Pt_3Sn$@$mSiO_2$ NPs in (FIG. 12A) pure methanol-$d_4$ (FIG. 12B) methanol-$d_4$ with pyridine-$d_5$ and (FIG. 12C) water-$d_2$ with pyridine-$d_5$ acquired immediately after bubbling p-$H_2$ at 350 mL/min for 20 s at different temperatures. Note that the top spectrum in (FIG. 12C) was obtained after bubbling p-$H_2$ at 120° C. instead of 105° C. The dotted lines highlight the chemical shift of dissolved $H_2$.
Figure 14:
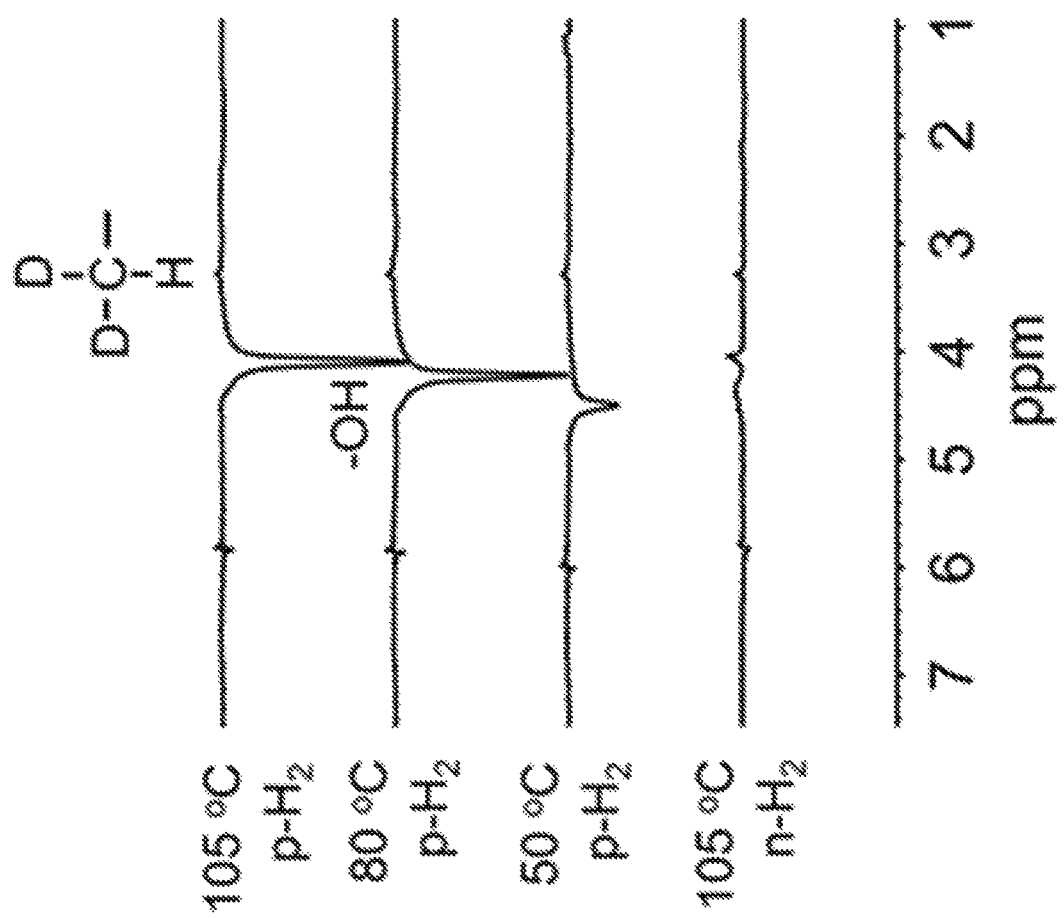
FIG. 14 is an example $^1H$ NMR spectra acquired using 50 mg $Pt_3Sn$@$mSiO_2$ NPs suspended in a mixture of methanol-$d_4$ and water-$d_2$ at a volume ratio of 1:1 after bubbling p-$H_2$ at 350 mL/min for 20 s at the indicated temperatures.

As the chemical shifts of the hydroxyl proton in methanol is commonly used as a calibration standard for temperature.[54] A peak shift as a function of temperature will confirm the chemical identity of hydroxyl proton. The temperature-dependent spectra of methanol without and with pyridine in the solution, respectively, are shown in FIG. 11. The chemical shift of the hyperpolarized signal in both sets of spectra show the same temperature-dependence. While the hyperpolarized signal shifts toward lower chemical shift, dissolved hydrogen molecule remains at 4.54 ppm (the slight variation of signal intensity arises from the different degree of relaxation during the manual sample transfer). Therefore, the intense hyperpolarized signal originates from the hydroxyl protons. The temperature-dependent spectra of water with dissolved pyridine are presented in FIG. 12C. The chemical shift of the protons in water shifts toward smaller values and the hyperpolarized signal intensity increases as temperature increases. A mixture of water and methanol also produces an intense hyperpolarized signal for the hydroxy/water exchanged protons at different temperatures (FIG. 14).

Magnetic Resonance Imaging Details.

The MR images were acquired with a standard SPIRAL-EPI acquisition, with a single 90° excitation pulse. The spiral trajectory was from the center of k-space out to maximize signal-to-noise in the images. The bandwidth of the excitation pulse was set to 2800 Hz to prevent excitation of the methanol present in the sample, this was achieved with a 0.45 W, 1.5 ms shaped excitation pulse. The images had an effective echo time of 1.24 ms, and were re-gridded using a previously acquired gradient trajectory to a 16×16 k-space matrix, before being Fourier transformed. The images had a slice thickness of 20 mm, with an in-plane isotropic field of view of 15×15 mm, leading to a pixel size of 0.94×0.94 mm. The total acquisition time of each image was 3.2 ms. The pulse shape and k-space re-gridding were calculated by the Bruker PV6.0.1 acquisition software. The phase used to color the images was calculated from the first recorded data point in the spiral acquisition, where no gradients are applied, and the signal is proportional to the total signal present in the sample.

TABLE 2

Substrates that did not exhibit a SWAMP effect using the experimental conditions herein.

| Substrate | Catalogue Number | Purity | % D | % $^{15}$N | Concentration | Solvent |
|---|---|---|---|---|---|---|
| D-(+)-Glucose | Sigma G8270 | ≥99.5% | 0 | N/A | 100 mM | D$_2$O |
| Glycine | Sigma-Aldrich G8898 | ≥99% | 0 | N/A | 100 mM | D$_2$O |
| Acetic Acid-d4 | Aldrich 233315 | ≥99% | ≥99.9% | N/A | pure | N/A |
| Pyridine ($^{15}$N) | Cambridge Isotope, NLM-305-0.5 | 98% | 0 | >98% | 100 mM | CD$_3$OD |
| Pyridine ($^{15}$N) | Cambridge Isotope, NLM-305-0.5 | 98% | 0 | >98% | 100 mM | D$_2$O |

Density Matrix Calculation Details (Derivation of Eq. 4).
The spin states of dihydrogen are the singlet-triplet states:

$$para\ |S_0\rangle = 2^{-1/2}(|\alpha\beta\rangle - |\beta\alpha\rangle) \quad (S1)$$

$$ortho\begin{cases} |T_1\rangle = |\alpha\alpha\rangle & (S2) \\ |T_0\rangle = 2^{-1/2}(|\alpha\beta\rangle + |\beta\alpha\rangle) \\ |T_{-1}\rangle = |\beta\beta\rangle \end{cases}$$

The density operators of pure p-H$_2$ and pure (unpolarized) o-H$_2$ are thus $$\hat{\rho}^{para} = |S_0\rangle\langle S_0| \quad (S3)$$

$$\hat{\rho}^{ortho} = \frac{1}{3}(|T_1\rangle\langle T_1| + |T_0\rangle\langle T_0| + |T_{-1}\rangle\langle T_{-1}|) \quad (S4)$$

For an arbitrary ortho-para mixture with para molecule fraction $x_p$:

$$\rho^{H_2} = x_p \hat{\rho}^{para} + (1-x_p)\hat{\rho}^{ortho} \quad (S5)$$

The spin Hamiltonian of H$_2$ suddenly changes upon dissociation into chemically inequivalent surface sites with chemical shifts $\omega_a^0$ and $\omega_b^0$, proton-proton and dipolar coupling $D_{ab}$. The spin Hamiltonian of the dipolar coupled H ad-atom pair takes the form $$\hat{\mathcal{H}}_{ads} = \omega_a^0 \hat{I}_{za} + \omega_b^0 \hat{I}_{zb} + D_{ab}(3\hat{I}_{za}\hat{I}_{zb} - \hat{I}_a \hat{I}_b) \quad (S6)$$

The eigenstates of $\hat{\mathcal{H}}_{ads}$ can in general be written $$|1\rangle = |\alpha\alpha\rangle \quad (S7)$$

$$|2\rangle = c_1|\alpha\beta\rangle + c_2|\beta\alpha\rangle \quad (S8)$$

$$|3\rangle = -c_2|\alpha\beta\rangle + c_1|\beta\alpha\rangle \quad (S8)$$

$$|4\rangle = |\beta\beta\rangle \quad (S10)$$

where $c_1 = \cos \kappa/2$, $c_2 = \sin \kappa/2$, $\tan \kappa = D_{ab}/\Delta_{ab}$ and $\Delta_{ab} = \omega_a^0 - \omega_b^0$. For weak coupling, $|D_{ab}| \ll |\Delta_{ab}|$ and $\kappa \to 0$ while for strong coupling, $|D_{ab}| \gg |\Delta_{ab}|$ and $\kappa \to \pm\pi/2$. For adsorption sites which render the two protons chemically equivalent, $\Delta_{ab}=0$. In the sudden approximation, the density matrix $\rho^{ads}$ of the H ad-atom pair is obtained by expressing $\hat{\rho}_{H_2}$ in the general eigenbasis. Off-diagonal elements of $\hat{\rho}^{ads}$ represent coherent superpositions of the eigenstates which may average due to the kinetic distribution of chemisorption events. This is modelled by time-averaging the density operator:

$$\bar{\rho}^{ads} = \int \rho^{ads} d\tau \quad (S11)$$

Due to the kinetic distribution of chemisorption events on time-scales large compared to the period of the coherence, $$\bar{\rho}_{23}^{ads} \to 0 \text{ and } \bar{\rho}_{32}^{ads} \to 0$$

are expected, leaving only diagonal elements to be calculated:

$$\bar{\rho}_{ii}^{ads} = \langle i|\hat{\rho}^{H_2}|i\rangle \quad (S12)$$

We obtain $$\bar{\rho}^{ads} = \frac{1}{3}\begin{pmatrix} 1-x_p & 0 & 0 & 0 \\ 0 & 1/2 + x_p & 0 & 0 \\ 0 & 0 & 1/2 + x_p & 0 \\ 0 & 0 & 0 & 1-x_p \end{pmatrix} + \quad (S13)$$

$$\frac{1}{6}\begin{pmatrix} 0 & 0 & 0 & 0 \\ 0 & 1-4x_p & 0 & 0 \\ 0 & 0 & -1+4x_p & 0 \\ 0 & 0 & 0 & 0 \end{pmatrix}\sin\kappa$$

In the oneH mechanism, a proton from the H ad-atom pair undergoes exchange with an —OD atom. For example, let the proton in site a be the one to undergo this exchange. The Zeeman order of the site-a proton abstracted into HDO will be calculated as well as the total proton Zeeman order for HD and HDO. We will calculate two observables, $\langle I_{za}\rangle (=Tr(I_{za} \cdot \bar{\rho}^{ads}))$ and $\langle \hat{I}_z \rangle (=Tr(I_z \cdot \bar{\rho}^{ads}))$, where $\hat{I}_z = \hat{I}_{za} + \hat{I}_{zb}$. Therefore, we express their matrix representations in the general basis.

$$I_{za} = \frac{1}{2}\begin{pmatrix} 1 & 0 & 0 & 0 \\ 0 & \cos\kappa & -\sin\kappa & 0 \\ 0 & -\sin\kappa & -\cos\kappa & 0 \\ 0 & 0 & 0 & 1 \end{pmatrix} \quad (S14)$$

$$\text{and } I_z = \begin{pmatrix} 1 & 0 & 0 & 0 \\ 0 & 0 & 0 & 0 \\ 0 & 0 & 0 & 0 \\ 0 & 0 & 0 & -1 \end{pmatrix} \quad (S15)$$

Lastly, the trace of the matrix product is obtained and reduced:

$$\langle I_{za}\rangle = Tr(I_{za} \cdot \bar{\rho}^{ads}) = \frac{1}{12}(1-4x_p)\sin(2\kappa) \quad (S16)$$

$$\langle \hat{I}_z \rangle = Tr(I_Z \cdot \bar{\rho}^{ads}) = 0 \quad (S17)$$

Therefore, $$P_{HDO} = 2\langle I_{za} \rangle = \frac{1}{6}(1 - 4x_p)\sin(2\kappa). \qquad \text{Eq. (4)}$$

If the remaining b proton recombines with the deuteron to form HD without significant relaxation, $$P_{HD} = -P_{HDO} \qquad \text{(S18)}$$

REFERENCES AND NOTES

1. Horke, D. A., Chang, Y.-P., Dlugolecki, K., and Küpper, J. (2014). Separating Para and Ortho Water. Angew Chem Int Ed 53, 11965-11968.
2. Kravchuk, T., Reznikov, M., Tichonov, P., Avidor, N., Meir, Y., Bekkerman, A., and Alexandrowicz, G. (2011). A Magnetically Focused Molecular Beam of Ortho-Water. Science 331, 319-321.
3. Tikhonov, V. I., and Volkov, A. A. (2002). Separation of Water into Its Ortho and Para Isomers. Science 296, 2363-2363.
4. Veber, S. L., Bagryanskaya, E. G., and Chapovsky, P. L. (2006). On the possibility of enrichment of $H_2O$ nuclear spin isomers by adsorption. JETP 102, 76-83.
5. Zhou, R., Zhao, E. W., Cheng, W., Neal, L. M., Zheng, H., Quiñones, R. E., Hagelin-Weaver, H. E., and Bowers, C. R. (2015). Parahydrogen-Induced Polarization by Pairwise Replacement Catalysis on Pt and Ir Nanoparticles. J Am Chem Soc 137, 1938-1946.
6. Meiboom, S. (1961). Nuclear Magnetic Resonance Study of the Proton Transfer in Water. J Chem Phys 34, 375-388.
7. Segawa, T., Kateb, F., Duma, L., Bodenhausen, G., and Pelupessy, P. (2008). Exchange Rate Constants of Invisible Protons in Proteins Determined by NMR Spectroscopy. ChemBioChem 9, 537-542.
8. Pei, Y., Maligal-Ganesh, R. V., Xiao, C., Goh, T.-W., Brashler, K., Gustafson, J. A., and Huang, W. (2015). An inorganic capping strategy for the seeded growth of versatile bimetallic nanostructures. Nanoscale 7, 16721-16728.
9. Maligal-Ganesh, R. V., Xiao, C., Goh, T. W., Wang, L.-L., Gustafson, J., Pei, Y., Qi, Z., Johnson, D. D., Zhang, S., Tao, F., et al. (2016). A Ship-in-a-Bottle Strategy To Synthesize Encapsulated Intermetallic Nanoparticle Catalysts: Exemplified for Furfural Hydrogenation. ACS Catal, 1754-1763.
10. Bowers, C. R., and Weitekamp, D. P. (1986). Transformation of Symmetrization Order to Nuclear-Spin Magnetization by Chemical-Reaction and Nuclear-Magnetic-Resonance. Phys Rev Lett 57, 2645-2648.
11. Bowers, C. R., and Weitekamp, D. P. (1987). Para-Hydrogen and Synthesis Allow Dramatically Enhanced Nuclear Alignment. J Am Chem Soc 109, 5541-5542.
12. Natterer, J. (1997). Thesis: NMR with Spin Polarized Molecules—Theory and Application. PhD.
13. Adams, R. W., Aguilar, J. A., Atkinson, K. D., Cowley, M. J., Elliott, P. I. P., Duckett, S. B., Green, G. G. R., Khazal, I. G., Lopez-Serrano, J., and Williamson, D. C. (2009). Reversible Interactions with para-Hydrogen Enhance NMR Sensitivity by Polarization Transfer. Science 323, 1708-1711.
14. Kovtunov, K. V., Beck, I. E., Bukhtiyarov, V. I., and Koptyug, I. V. (2008). Observation of Parahydrogen-Induced Polarization in Heterogeneous Hydrogenation on Supported Metal Catalysts. Angew Chem Int Ed 47, 1492-1495.
15. Duckett, S. B., and Mewis, R. E. (2012). Application of Parahydrogen Induced Polarization Techniques in NMR Spectroscopy and Imaging. Accounts Chem Res 45, 1247-1257.
16. Franzoni, M. B., Graafen, D., Buljubasich, L., Schreiber, L. M., Spiess, H. W., and Munnemann, K. (2013). Hyperpolarized H-1 long lived states originating from parahydrogen accessed by rf irradiation. PCCP 15, 17233-17239.
17. Shchepin, R. V., Barskiy, D. A., Coffey, A. M., Esteve, I. V. M., and Chekmenev, E. Y. (2016). Efficient Synthesis of Molecular Precursors for Para-Hydrogen-Induced Polarization of Ethyl Acetate-1-C-13 and Beyond. Angew Chem Int Ed 55, 6071-6074.
18. Colell, J. F. P., Emondts, M., Logan, A. W. J., Shen, K., Bae, J., Shchepin, R. V., Ortiz, G. X., Spannring, P., Wang, Q., Malcolmson, S. J., et al. (2017). Direct Hyperpolarization of Nitrogen-15 in Aqueous Media with Parahydrogen in Reversible Exchange. J Am Chem Soc.
19. Barskiy, D. A., Kovtunov, K. V., Koptyug, I. V., He, P., Groome, K. A., Best, Q. A., Shi, F., Goodson, B. M., Shchepin, R. V., Coffey, A. M., et al. (2014). The Feasibility of Formation and Kinetics of NMR Signal Amplification by Reversible Exchange (SABRE) at High Magnetic Field (9.4 T). J Am Chem Soc 136, 3322-3325.
20. Colell, J. F. P., Logan, A. W. J., Zhou, Z. J., Shchepin, R. V., Barskiy, D. A., Ortiz, G. X., Wang, Q., Malcolmson, S. J., Chekmenev, E. Y., Warren, W. S., et al. (2017). Generalizing, Extending, and Maximizing Nitrogen-15 Hyperpolarization Induced by Parahydrogen in Reversible Exchange. J Phys Chem C 121, 6626-6634.
21. Lehmkuhl, S., Emondts, M., Schubert, L., Spannring, P., Klankermayer, J., Bltimich, B., and Schleker, P. P. M. (2017). Hyperpolarizing Water with Parahydrogen. ChemPhysChem 18, 2426-2429.
22. Zhao, E. W., Maligal-Ganesh, R., Xiao, C., Goh, T.-W., Qi, Z., Pei, Y., Hagelin-Weaver, H. E., Huang, W., and Bowers, C. R. (2017). Silica-Encapsulated Pt—Sn Intermetallic Nanoparticles: A Robust Catalytic Platform for Parahydrogen-Induced Polarization of Gases and Liquids. Angew Chem Int Ed 56, 3925-3929.
23. Fearon, J., and Watson, G. W. (2006). Hydrogen adsorption and diffusion on Pt {111} and PtSn {111}. J Mater Chem 16, 1989-1996.
24. Samson, P., Nesbitt, A., Koel, B., and Hodgson, A. (1998). Deuterium dissociation on ordered Sn/Pt (111) surface alloys. J Chem Phys 109, 3255-3264.
25. Voss, M. R., Busse, H., and Koel, B. E. (1998). Adsorption of thermal D atoms on Sn/Pt(111) surface alloys. Surf Sci 414, 330-340.
26. d-methanol, Cambridge Isotopes, DLM-24-10 (D, 99.8%), 99.5% chemical purity.
27. d-ethanol, Sigma Aldrich, 186414-5G (D>99.5%), 99.9% chemical purity.
28. Levitt, M. H. (2013). Spectroscopy of light-molecule endofullerenes. Philos Trans R Soc Lond B Biol Sci. 371.
29. Oddershede, J., Geertsen, J., and Scuseria, G. E. (1988). Nuclear spin-spin coupling constant of hydrogen molecule with deuterium (HD). J Phys Chem 92, 3056-3059.
30. Panja, C., Saliba, N., and Koel, B. E. (1998). Adsorption of methanol, ethanol and water on well-characterized Pt—Sn surface alloys. Surf Sci 395, 248-259.
31. McBride, F., Darling, G. R., Pussi, K., and Hodgson, A. (2011). Tailoring the Structure of Water at a Metal Surface: A Structural Analysis of the Water Bilayer Formed on an Alloy Template. Phys Rev Lett 106.
32. McBride, F., Darling, G. R., Pussi, K., Lucas, C. A., Grunder, Y., Darlington, M., Brownrigg, A., and Hodgson, A. (2013). The Influence of Water and Hydroxyl on a Bimetallic (root 3×root 3)R30 degrees Sn/Pt Surface Alloy. J Phys Chem C 117, 4032-4039.
33. Paffett, M. T., Gebhard, S. C., Windham, R. G., and Koel, B. E. (1990). Chemisorption of carbon monoxide, hydrogen, and oxygen on ordered tin/platinum(111) surface alloys. J Phys Chem 94, 6831-6839.
34. Pan, M., Pozun, Z. D., Yu, W. Y., Henkelman, G., and Mullins, C. B. (2012). Structure Revealing H/D Exchange with Co-Adsorbed Hydrogen and Water on Gold. J Phys Chem Lett 3, 1894-1899.
35. Chen, N., Blowers, P., and Masel, R. I. (1999). Formation of hydronium and water-hydronium complexes during coadsorption of hydrogen and water on (2×1)Pt(110). Surf Sci 419, 150-157.
36. Lackey, D., Schott, J., Sass, J. K., Woo, S. I., and Wagner, F. T. (1991). Surface-science simulation study of the electrochemical charge-transfer reaction (H)ad+($H_2O$)ad→($H_3O+$)ad +e-metal on Pt(111) and Cu(110). Chem Phys Lett 184, 277-281.
37. Permin, A. B., and Eisenberg, R. (2002). One-Hydrogen Polarization in Hydroformylation Promoted by Platinum-Tin and Iridium Carbonyl Complexes: A New Type of Parahydrogen-Induced Effect. J Am Chem Soc 124, 12406-12407.
38. Ivanov, K. L., Pravdivtsev, A. N., Yurkovskaya, A. V., Vieth, H.-M., and Kaptein, R. (2014). The role of level anti-crossings in nuclear spin hyperpolarization. PROG NUCL MAG RES SP 81, 1-36.
39. Aime, S., Gobetto, R., and Canet, D. (1998). Longitudinal Nuclear Relaxation in an A2 Spin System Initially Polarized through Para-Hydrogen. J Am Chem Soc 120, 6770-6773.
40. Carson, P. J., Bowers, C. R., and Weitekamp, D. P. (2001). The PASADENA Effect at a Solid Surface: High-Sensitivity Nuclear Magnetic Resonance of Hydrogen Chemisorption. J Am Chem Soc 123, 11821-11822.
41. Knecht, S., Pravdivtsev, A. N., Hovener, J.-B., Yurkovskaya, A. V., and Ivanov, K. L. (2016). Quantitative description of the SABRE process: rigorous consideration of spin dynamics and chemical exchange. RSC Adv 6, 24470-24477.
42. Knecht, S., Kiryutin, A. S., Yurkovskaya, A. V., and Ivanov, K. L. (2018). Mechanism of spontaneous polarization transfer in high-field SABRE experiments. J Magn Reson 287, 74-81.
43. Moreno, K. X., Nasr, K., Milne, M., Sherry, A. D., and Goux, W. J. (2015). Nuclear spin hyperpolarization of the solvent using signal amplification by reversible exchange (SABRE). J Magn Reson 257, 15-23.
44. Dücker, E. B., Kuhn, L. T., Münnemann, K., and Griesinger, C. (2012). Similarity of SABRE field dependence in chemically different substrates. J Magn Reson 214, 159-165.
45. Ardenkjær-Larsen, J. H., Fridlund, B., Gram, A., Hansson, G., Hansson, L., Lerche, M. H., Servin, R., Thaning, M., and Golman, K. (2003). Increase in signal-to-noise ratio of >10,000 times in liquid-state NMR. Proceedings of the National Academy of Sciences 100, 10158-10163.
46. Mammoli, D., Salvi, N., Milani, J., Buratto, R., Bornet, A., Sehgal, A. A., Canet, E., Pelupessy, P., Carnevale, D., Jannin, S., et al. (2015). Challenges in preparing, preserving and detecting para-water in bulk: overcoming proton exchange and other hurdles. PCCP 17, 26819-26827.
47. Chappuis, Q., Milani, J., Vuichoud, B., Bornet, A., Gossert, A. D., Bodenhausen, G., and Jannin, S. (2015). Hyperpolarized Water to Study Protein—Ligand Interactions. J Phys Chem Lett 6, 1674-1678.
48. Lingwood, M. D., Siaw, T. A., Sailasuta, N., Abulseoud, O. A., Chan, H. R., Ross, B. D., Bhattacharya, P., and Han, S. (2012). Hyperpolarized Water as an MR Imaging Contrast Agent: Feasibility of in Vivo Imaging in a Rat Model. Radiology 265, 418-425.
49. McCarney, E. R., Armstrong, B. D., Lingwood, M. D., and Han, S. (2007). Hyperpolarized water as an authentic magnetic resonance imaging contrast agent. Proc Natl Acad Sci USA 104, 1754-1759.
50. Harris, T., Szekely, O., and Frydman, L. (2014). On the Potential of Hyperpolarized Water in Biomolecular NMR Studies. J Phys Chem B 118, 3281-3290.
51. Ahn, C. B., H., K. J., and H., C. Z. (1986). High-Speed Spiral-Scan Echo Planar NMR Imaging-I. IEEE T MED IMAGING 5, 6.
52. Espy, M., Matlashov, A., and Volegov, P. (2013). SQUID-detected ultra-low field MRI. J Magn Reson 229, 127-141.
53. Iali, W., Olaru, A M., Green, G. G. R., and Duckett, S. B. (2017). Achieving High Levels of NMR-Hyperpolarization in Aqueous Media With Minimal Catalyst Contamination Using SABRE. Chem-Eur J 23, 10491-10495.
54. Raiford, D. S., Fisk, C. L., and Becker, E. D. (1979). Calibration of methanol and ethylene glycol nuclear magnetic resonance thermometers. Anal Chem 51, 2050-2051.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

Many variations and modifications may be made to the above-described embodiments. All such modifications and variations are intended to be included herein within the scope of this disclosure and protected by the following claims.

We claim:

1. A method of making a hyperpolarized fluid, comprising:
exposing a fluid and parahydrogen to a catalyst, where the fluid is a liquid or a gas and where the catalyst is an intermetallic nanoparticle heterogeneous catalyst and comprises cube, octahedron, or rod-shaped $CeO_2$ nanocrystals, wherein the fluid is selected from the group consisting of: water, methanol, ethanol, propanol, methylamine, ammonia, ethaneamide, methanamide, and a combination thereof;
making hyperpolarized fluid upon an interaction of the fluid, the parahydrogen, and the catalyst, wherein the catalyst has surface properties that restrict diffusion of hydrogen ad-atoms, and wherein the interaction does not result in hydrogenation of the fluid;

introducing the hyperpolarized fluid to a subject for the purpose of renal or coronary angiography, wherein the hyperpolarized fluid is a contrast agent; and acquiring an image of subject using an imaging device.

2. The method of claim 1, wherein the exposing comprises one of:

mixing the fluid with the catalyst to produce a fluid-catalyst mixture and dissolution of parahydrogen into the fluid-catalyst mixture;

dissolving the parahydrogen with the fluid to form a fluid-parahydrogen mixture and mixing the fluid-parahydrogen mixture with the catalyst; or exposing the fluid in a vapor state and parahydrogen to the catalyst to form a hyperpolarized fluid in a vaporized state.

3. The method of claim 1, wherein the catalyst is a Group VIII, IB, or 11B transition metal-based catalyst including Ce and at least one other metal.

4. The method of claim 1, wherein the catalyst comprises Ce and at least one of Pt, Pd, Cu, Au, Ag, Rh, Ru, Ir, Ni, Sn, Co, Zn, Ti, Al, Fe, Si or O.

5. The method of claim 1, wherein the catalyst is a bimetallic catalyst comprised of supported single atoms, pairs of atoms, clusters or intermetallic nanoparticles.

6. The method of claim 1, wherein the catalyst is insoluble in the fluid, an emulsion, or a suspension of insoluble intermetallic nanoparticles.

7. A method of making a hyperpolarized fluid, comprising:

exposing a fluid and parahydrogen to a catalyst, where the fluid is a liquid or a gas and where the catalyst is an intermetallic nanoparticle heterogeneous catalyst and comprises cube, octahedron, or rod-shaped $CeO_2$ nanocrystals, wherein the fluid comprises water diluted in an aprotic solvent, wherein the aprotic solvent is selected from the group consisting of dioxane, nitromethane, acetonitrile, acetone, dichloromethane, and a combination thereof, in their per-deuterated or partially deuterated forms;

making hyperpolarized fluid upon an interaction of the fluid, the parahydrogen, and the catalyst, wherein the catalyst has surface properties that restrict diffusion of hydrogen ad-atoms, and wherein the interaction does not result in hydrogenation of the fluid;

introducing the hyperpolarized fluid to a subject for the purpose of renal or coronary angiography, wherein the hyperpolarized fluid is a contrast agent; and acquiring an image of subject using an imaging device.

8. A method of making a hyperpolarized fluid, comprising:

exposing a fluid and parahydrogen to a catalyst, where the fluid is a liquid or a gas and where the catalyst is an intermetallic nanoparticle heterogeneous catalyst and comprises cube, octahedron, or rod-shaped $CeO_2$ nanocrystals, wherein the fluid is selected from the group consisting of: water, methanol, ethanol, propanol, methylamine, ammonia, ethaneamide, methanamide, and a combination thereof;

making hyperpolarized fluid upon an interaction of the fluid, the parahydrogen, and the catalyst, wherein the catalyst has surface properties that restrict diffusion of hydrogen ad-atoms, and wherein the interaction does not result in hydrogenation of the fluid; and condensing the hyperpolarized fluid as a hyperpolarized solid.

* * * * *